(12) United States Patent
Gauduin et al.

(10) Patent No.: US 9,730,996 B2
(45) Date of Patent: Aug. 15, 2017

(54) INVOLUCRIN-DRIVEN RETROVIRAL EXPRESSION CASSETTES ENCODING HUMAN IMMUNODEFICIENCY VIRUS ENVELOPE GLYCOPROTEINS

(71) Applicant: Texas Biomedical Research Institute, San Antonio, TX (US)

(72) Inventors: Marie-Claire Gauduin, Helotes, TX (US); Philippe Blancou, Riaille (FR)

(73) Assignee: Texas Biomedical Research Institute, San Antonio, TX (US)

( * ) Notice: Subject to any disclaimer, the term of this patent is extended or adjusted under 35 U.S.C. 154(b) by 4 days.

(21) Appl. No.: 14/062,125

(22) Filed: Oct. 24, 2013

(65) Prior Publication Data

US 2014/0178426 A1    Jun. 26, 2014

Related U.S. Application Data

(60) Provisional application No. 61/632,431, filed on Oct. 24, 2012, provisional application No. 61/793,658, filed on Mar. 15, 2013.

(51) Int. Cl.
| | |
|---|---|
| C12N 15/86 | (2006.01) |
| A61K 39/12 | (2006.01) |
| C12N 15/00 | (2006.01) |
| A61K 39/00 | (2006.01) |

(52) U.S. Cl.
CPC .............. *A61K 39/12* (2013.01); *C12N 15/86* (2013.01); *A61K 2039/523* (2013.01); *A61K 2039/5256* (2013.01); *A61K 2039/53* (2013.01); *A61K 2039/55566* (2013.01); *C12N 15/00* (2013.01); *C12N 2740/15034* (2013.01); *C12N 2740/15041* (2013.01)

(58) Field of Classification Search
CPC ............ A61K 39/12; A61K 2039/5256; C12N 15/86; C12N 2740/15041
See application file for complete search history.

(56) References Cited

U.S. PATENT DOCUMENTS

| | | | |
|---|---|---|---|
| 5,571,712 A * | 11/1996 | Haynes et al. | ................ 435/364 |
| 6,313,373 B1 | 11/2001 | Eckert et al. | |
| 6,521,457 B2 | 2/2003 | Olsen | |
| 6,555,107 B2 | 4/2003 | Poeschia et al. | |
| 7,632,509 B2 | 12/2009 | Fang et al. | |
| 7,785,870 B2 | 8/2010 | Takahashi et al. | |

OTHER PUBLICATIONS

Ghazizadeh, S., et al., 2002, Durablbe and stratum-specific gene expression in epidermis, Gene Therapy 9:1278-1285.*
Lohman, B. L., et al., Dec. 1995, Antiviral cytotoxic T lymphocytes in vaginal mucosa of simian immunodeficiency virus-infected-rhesus macaques, J. Immunol. 155(12):5855-5860.*
Evans, D. T., et al., Jun. 2005, Immunization of macaques with single-cycle simian immunodeficiency virus (SIV) stimulates diverse virus-specific immune responses and reduces viral loads after challenge with SIVmac230, J. Virol. 79(12):7707-7720.*
Ghazizadeh, S., et al., 2002, Durable and stratum-specific gene expression in epidermis, Gene Therapy 9:1278-1285.*
Kozlowski, P. A., May 2003, The role of mucosal immunity in prevention of HIV transmission, Curr. Mol. Med. 3(3):217-228 (abstract provided).*
Igarashi, T., et al., 1997, Protection of monkeys vaccinated with vpr- and/or nef-defective simian immunodeficiency virus strain mac/human immunodeficiency virus type 1 chimeric viruses: a potential candidate live-attenuated human AIDS vaccine, J. Gen. Virol. 78:985-989.*
Andersen, B., et al., Skn-1a and Skn-1i: Two Functionally Distinct Oct-2-Related Factors Expressed in Epidermis; Science, Apr. 2, 1993; pp. 78-82; vol. 260.
Byrne, C., et al., Probing Keratinocyte and Differentiation Specificity of the Human K5 Promoter in Vitro and in Transgenic Mice; Molecular and Cellular Biology; 1993; pp. 3176-3190; vol. 13, No. 6; Journals.ASM.org.
Crish, J. F., et al., Tissue-Specific and Differentiation-Appropriate Expression of the Human Involucrin Gene in Transgenic Mice: an Abnormal Epidermal Phenotype; Differentiation; 1993; pp. 191-200; vol. 53; Springer-Verlag.
Daniel, M. D., et al., Protective Effects of a Live Attenuated SIV Vaccine with a Deletion in the nef Gene; Science, Dec. 18, 1992; pp. 1938-1941; vol. 258.
DiSepio, D., et al., Characterization of Ioricrin Regulation in Vitro and in Transgenic Mice; Differentiation; 1999; pp. 225-235; vol. 64; Springer-Verlag.
Eckert, R. L., Structure, Function, and Differentiation of the Keratinocyte; Physiological Reviews; Oct. 1989, pp. 1316-1346; vol. 69, No. 4.; The American Physiological Society.
Emerman, M., et al., Genes with Promoters in Retrovirus Vectors can be Independently Suppressed by an Epigenetic Mechanism; Cell Growth Differentiation; Dec. 1964; pp. 459-467; vol. 39, (Part 2); MIT.
Fuchs, E., Epidermal Differentiation; Current Opinion in Cell Biology; 1990; pp. 1028-1035; vol. 2; Current Biology, Ltd.

(Continued)

*Primary Examiner* — Jeffrey Parkin
(74) *Attorney, Agent, or Firm* — Bracewell LLP; Karthika Perumal

(57) ABSTRACT

The present invention provides for novel compositions and methods for delivering genes of interest to stem cells using vectors that contain differentiation-specific transcriptional regulatory elements. For example, stem cells in the internal epithelia could be transfected with a vaccine construct, which has an epithelial cell differentiation-specific promoter driving the expression of viral envelope proteins. When the promoter used is specific for terminally differentiated epithelial cells, then the viral envelope proteins will be expressed only in the upper part of the epithelia and therefore, stimulate the immune response. The infected epithelial stem cells in the basal layer will continue to produce new antigen-expressing cells, without being eliminated by the immune response. This invention will be useful in the development of vaccines against viral agents that target the internal mucosa like HIV.

15 Claims, 15 Drawing Sheets

(56) References Cited

OTHER PUBLICATIONS

Gauduin, M-C., et al., Optimization of Intracellular Cytokine Staining for the Quintitation of Antigen-Specific CD4+ T Cell Responses in Rhesus Macaques; Journal of Immunological Methods, 2004; pp. 61-79; vol. 288; Elsevier B.V.

Gibbs, J. S., Construction and In Vitro Properties of SIV mac Mutants with Deletions in "Nonessential" Genes; AIDS Research and Human Retroviruses; Nov. 5, 1994; pp. 607-616; vol. 10, No. 5; Mary Ann Liebert, Inc.

Green, H., et al., Regulation by Vitatim A of Envelope Cross-Linking in Cultured Keratinocytes Derived from Different Human Epithelia; Molecular and Cellular Biology; 1982; p. 1115; vol. 2, No. 9; Journals.ASM.org.

Gross, M., et al., Isolation, Characterization, and In Vitro Cultivation of Keratinocyte Subfractions from Adult NMRI Mouse Epidermis: Epidermal Target Cells for Phorbol Esters; Experimental Cell Research; 1987; pp. 460-474; vol. 171, No. 2; American Press, Inc.

Lapres, J. J., et al., Nucleic Acids, Protein Synthesis, and Molecular Genetics: Identification of a Functional Determinant of Differentiation-Dependent Expression in the Involucrin Gene; The Journal of Biological Chemistry; 1996; pp. 23154-23160; vol. 271; American Society for Biochemistry and Molecular Biology.

Jang, S-I., et al., Nucleic Acids, Protein Synthesis, and Moleclar Genetics: Activator Protein 1 Activity is Involved in the Regulation of the Cell type-Specific Expression from the Proximal Promoter of the Human Profilaggrin Gene; The Journal of Biological Chemistry; 1996; pp. 24105-24114; vol. 271; American Society for Biochemistry and Molecular Biology.

Johnson, W. E., et al., Viral Persistence: HIV's Strategies of Immune System Evasion; Annual Reviews Medicine; 2002; pp. 499-518; vol. 53; Annual Reviews.

Klumpp, D. J., et al., Differentiation-Induced Changes in Promoter Usage for Transcripts Encoding the Human Papillomavirus Type 31 Replication Protein E1; Virology; 1999; pp. 239-246; vol. 257; Academic Press.

Kobayashi, T., et al., Immunolocalizations of Human Gelatinase (Type IV Collagenase, MMP-9) and TIMP (Tissue Inhibitor of Metalloproteinases) in Normal Epidermis and some Epidermal Tumors; Arch Dermatol Research; 1996; pp. 239-244; vol. 288; Springer-Verlag.

Lopez-Bayghen, E., et al., Nucleic Acids, Protein Synthesis, and Molecular Genetics: Transcriptional Analysis of the 5'-Noncoding Region of the Human Involucrin Gene; The Journal of Biological Chemistry; 1996; pp. 512-520; vol. 271; American Society for Biochemistry and Molecular Biology.

Mikszta, J. A., et al., Improved Genetic Immunization via Micromechanical Disruption of Skin-Barrier Function and Targeted Epidermal Delivery; Nature Medicine; Apr. 2002; pp. 415-419; vol. 8, No. 4; Nature Publishing Group; http://medicine.nature.com.

Miller, N., et al., Progress in Transcriptionally Targeted and Regulatable Vectors for Genetic Therapy; Human Gene Therapy; May 1, 1997; pp. 803-815; vol. 8; Mary Ann Liebert, Inc.

Ng, D. C., et al., Genes: Structure and Regulation: Requirement of an Al-1 Site in the Calcium Response Region of the Involucrin Promoter; The Journal of Biological Chemistry; 2000; pp. 24080-24088; vol. 275; American Society for Biochemistry and Molecular Biology.

Parker, J. N., et al., Mutational Analyses of Differentiation-Dependent Human Papillomavirus Type 18 Enhancer Elements in Epithelial Raft Cultures of Neonatal Foreskin Keratinocytes; Cell Growth & Differentiation; Jul. 1997; pp. 751-762; vol. 8.

Reid, C. B. A., et al., A Simple and Reliable Technique for Culturing of Human Oral Keratinocytes and Fibroblasts; Acta Otolaryngol; 1997; pp. 628-633; vol. 117, No. 4; Scandinavian University Press.

Roop, D. R., et al., Transcriptional Control of High Molecular Weight Keratin Gene Expression in Multistage Mouse Skin Carcinogenesis; Cancer Research; 1988; pp. 3245-3252; vol. 48; American Association for Cancer Research.

Veazey, R. S., et al., The Mucosal Immune System: Primary Target for HIV Infection and AIDS; Trends in Immunology; Nov. 2001; pp. 626-633; vol. 22, No. 11; Elsevier Science, Ltd.

Welter, J. F., et al., Differential Expression of the fos and jun Family Members c-fos, fosB, Fra-1, Fra-2, c-jun, junB and JunD During Human Epidermal Keratinocyte Differentiation; Oncogene; 1995; pp. 2681-2687; vol. 11; Stockton Press.

Yuzawa, K., et al., APC0576: A Novel Small Molecule Immunosuppressive Agent Effective in Primate Models; Transplantation; May 15, 2003; pp. 1463-1468; vol. 75, No. 9; Lippincott Williams & Wilkins, Inc.

Germain, L., et al., Improvement of Human Keratinocyte Isolation and Culture Using Thermolysin; Burns; 1993; pp. 99-104; vol. 19, No. 2; Butterworth-Heinemann, Ltd.

Gauduin, M-C., et al., Immunization with Live Attenuated Simian Immunodeficiency Virus Induces Strong Type 1 T Helper Responses and B-Chemokine Production; Proc. Nat. Acad. Sci. USA; Nov. 23, 1999; pp. 14031-14036; vol. 96, No. 24.

Ghazizadeh, S., et al., Durable and Stratum-Specific Gene Expression in Epidermis; Gene Therapy (Research Article); May 7, 2002; pp. 1278-1285; vol. 9; Nature Publishing Group; www.nature.com/gt.

Grande, A., et al., Transcriptional Targeting of Retroviral Vectors to the Erythroblastic Progeny of Transduced Hematopoietic Stem Cells; Gene Therapy (Blood); May 15, 1999; pp. 3276-3285; vol. 93, No. 10; The American Society of Hematology.

Higgins, G. D., et al., Transcription Patterns of Human Papillomavirus Type 16 in Genital Intraepithelial Neoplasia: Evidence for Promoter Usage Within the E7 Open Reading Frame During Epithelial Differentiation; Journal of General Virology; 1992; pp. 2047-2057; vol. 73.

Kobayashi, T., et al., A Novel Mechanism of Matrix Metalloproteinase-9 Gene Expression Implies A Role for Keratinization; EMBO Reports (Scientific Report); 2001; pp. 604-608; vol. 2, No. 7; European Molecular Biology Organization.

Kolodka, T. M., et al., Evidence for Keratinocyte Stem Cells in Vitro: Long Term Engraftment and Persistence of Transgene Expression from Retrovirus-Transduced Keratinocytes; Proc. Nat. Acad. Sci. USA (Cell Biology); Apr. 1998; pp. 4356-4361; vol. 95; The National Academy of Sciences.

Leask, A., et al., Transcription Factor AP2 and its Role in Epidermal-Specific Gene Expression; Proc. Nat. Acad. Sci. USA (Biochemistry); Sep. 1991; pp. 7948-7952; vol. 88.

Leask, A., et al., Regulation of a Human Epidermal Keratin Gene: Sequences and Nuclear Factors Involved in Keratinocyte-Specific Transcription; Genes & Development; 1990; pp. 1985-1998; vol. 4; Cold Spring Harbor Laboratory Press.

Lohman, B. L., et al., Antiviral Cytotoxic T Lymphocytes in Vaginal Mucosa of Simian Immunodeficiency Virus-Infected-Rhesus Macaques 1; The Journal of Immunology; Dec. 15, 1995; pp. 5855-5860; vol. 155, No. 12; The American Association of Immunologists.

Mathor, M. B., et al., Clonal Analysis of Stably Transduced Human Epidermal Stem Cells in Culture; Proc. Nat. Acad. Sci. USA (Medical Sciences); Sep. 1996; pp. 10371-10376; vol. 93.

Maytin, E. V., et al., Keratin 10 Gene Expression During Differentiation of Mouse Epidermis Requires Transcription Factors C/EBP and AP-2; Development Biology; 1999; pp. 164-181; vol. 216; Academic Press.

Rossi, A., et al., Effect of AP1 Transcription Factors on the Regulation of Transcription in Normal Human Epidermal Keratinocyres; The Society for Investigative Dermatology, Inc.; 1998; pp. 34-40; vol. 110.

Wyand, M. S., et al., Vaccine Protection by a Triple Deletion Mutant of Simian Immunodeficiency Virus; Journal of Virology; Jun. 1996; pp. 3724-3733; vol. 70, No. 6; American Society of Microbiology.

Zhang, Z.-Q., et al., Sexual Transmission and Propagation of SIV and HIV in Resting and Activated CD4+ T Cells; Science, Nov. 12, 1999; pp. 1353-1357; vol. 286.

(56) References Cited

OTHER PUBLICATIONS

Gordon, S. N., et al., Targeting the Vaginal Mucosa with Human Papillomavirus Pseudovirion Vaccines Delivering Simian Immunodeficiency Virus DNA; The Journal of Immunology; 2012; pp. 714-723; vol. 188.
Agarwal, C., et al., CCAAT/Enhancer-Binding Proteins: A Role in Regulation of Human Involucrin Promoter Response to Phorbol Ester; The Journal of Biological Chemistry; 1999; pp. 6190-6194; vol. 274 No. 10.
Ai, W., et al., CCAAT Displacement Protein Binds to and Negatively Regulates Human Papillomavirus Type 6 E6, E7, and E1 Promoters; Journal of Virology; 1999; pp. 4220-4229; vol. 73 No. 5.
Ai, W., et al., Yin Yang 1 Negatively Regulates the Differentiation-Specific E1 Promoter of Human Papillomavirus Type 6; Journal of Virology; 2000; pp. 5198-5205; vol. 74 No. 11.
Almond, N., et al., Protection by Attenuated Simian Immunodeficiency Virus in Macaques Against Challenge With Virus-Infected Cells; Lancet; May 27, 1995; pp. 1342-1344; vol. 345 Issue 8961.
Andersen, B., et al., Functions of the POU Domain Genes Skn-1a/i and Tst 1/Oct-6/SCIP in Epidermal Differentiation; Genes & Development; 1997; pp. 1873-1884; vol. 11; Cold Spring Harbor Laboratory Press.
Belyakov, I. M., et al., Mucosal AIDS Vaccine Reduces Disease and Viral Load in Gut Reservoir and Blood After Mucosal Infection of Macaques; Nature Medicine, Dec. 2001; pp. 1320-1326; vol. 7 No. 12; Nature Publishing Group.
Blancou, P., et al., Simian Immunodeficiency Virus Promoter Exchange Results in a Highly Attenuated Strain that Protects Against Uncloned Challenge Virus; Journal of Virology; 2004; pp. 1080-1092; vol. 78 No. 3.
Byrne, C., Programming Gene Expression in Developing Epidermis; Development; 1994; pp. 2369-2383; vol. 120 No. 9.
Carroll, J. M., et al., Tissue- and Stratum-Specific Expression of the Human Involucrin Promoter in Transgenic Mice; Proceedings of the National Academy of Sciences of the USA; Nov. 1993; pp. 10270-10274; vol. 90.
Chang, L. J., et al., Human Immunodeficiency Viruses Containing Heterologous Enhancer/Promoters are Replication Competent and Exhibit Different Lymphocyte Tropisms; Journal of Virology; 1993; pp. 743-752; vol. 67 No. 2.
Cranage, M. P., et al., Macaques Infected with Live Attenuated SIVmac are Protected Against Superinfection via the Rectal Mucosa; Journal of Virology; 1997; pp. 143-154; vol. 229; Academic Press.
Crish, J. F., et al., Nucleic Acids, Protein Synthesis, and Molecular Genetics: The Distal Regulatory Region of the Human Involucrin Promoter is Required for Expression in Epidermis; The Journal of Biological Chemistry; 1998; pp. 30460-30465; vol. 273.
Cromwell, M. A., et al., Induction of Mucosal Homing Virus-Specific CD8+ T Lymphocytes by Attenuated Simian Immunodeficiency Virus; Journal of Virology; 2000; pp. 8762-8766; vol. 74 No. 18.
Cromwell, M. A., SIV-Specific CD8* T Cells are Enriched in Female Genital Mucosa of Rhesus Macaques and Express Receptors for Inflammatory Chemokines; American Journal of Reproductive Immunology; 2011; pp. 242-247; vol. 65; John Wiley & Sons A/S.

Desrosiers, R. C., et al., Strategies Used by Human Immunodeficiency Virus that Allow Persistent Viral Replication; Nature Medicine: Jul. 1999; pp. 723-725; vol. 5 No. 7.
Diaz, R. M., et al., Exchange of Viral Promoter/Enhancer Elements with Heterologous Regulatory Sequences Generates Targeted Hybrid Long Terminal Repeat Vectors for Gene Therapy of Melanoma; Journal of Virology; 1998; pp. 789-795; vol. 72 No. 1.
Evans, D. T., et al., Mucosal Priming of Simian Immunodeficiency Virus-Specific Cytotoxic T-Lymphocyte Responses in Rhesus Macaques by the Salmonella Type III Secretion Antigen Delivery System; Journal of Virology; 2003; pp. 2400-2409; vol. 77 No. 4.
Fischer, D. F., et al., Interdependent Transcription Control Elements Regulate the Expression of the SPRR2A Gene During Keratinocyte Terminal Differentiation; Molecular and Cellular Biology; 1996; pp. 5365-5374; vol. 16 No. 10.
Fuchs, E., Epidermal Differentiation: The Bare Essentials; The Journal of Cell Biology; Dec. 1990; pp. 2807-2814; vol. 111 No. 6 Pt. 2; The Rockefeller University Press.
Grassmann, K., et al., Identification of a Differentiation-Inducible Promoter in the E7 Open Reading Frame of Human Papillomavirus Type 16 (HPV-16) in Raft Cultures of a New Cell Line Containing High Copy Numbers of Episomal HPV-16 DNA; Journal of Virology; 1996; pp. 2339-2349; vol. 70 No. 4.
Hu, J., et al., Simian Immunodeficiency Virus Rapidly Penetrates the Cervicovaginal Mucosa After Intravaginal Inoculation and Infects Intraepithelial Dendritic Cells; Journal of Virology; 2000; pp. 6087-6095; vol. 74 No. 13.
Hummel, M., et al., Differentiation-Induced and Constitutive Transcription of Human Papillomavirus Type 31b in Cell Lines Containing Viral Episomes; Journal of Virology; 1992; pp. 6070-6080; vol. 66 No. 10.
Johnson, R. P., et al., Highly Attenuated Vaccine Strains of Simian Immunodeficiency Virus Protect Against Vaginal Challenge; Inverse Relationship of Degree of Protection with Level of Attenuation; Journal of Virology; 1999; pp. 4952-4961; vol. 73 No. 6.
Kukimoto, I., et al., Displacement of YY1 by Differentiation-Specific Transcription Factor hSkn-1a Activates the P670 Promoter of Human Papillomavirus Type 16; Journal of Virology; 2001; pp. 9302-9311; vol. 75 No. 19.
Ozbun M. A., et al., Characterization of Late Gene Transcripts Expressed During Vegetative Replication of Human Papillomavirus Type 31b; Journal of Virology; 1997; pp. 5161-5172; vol. 71 No. 7.
Ruesch, M. N., et al., Activation of Papillomavirus Late Gene Transcription and Genome Amplification Upon Differentiation in Semisolid Medium is Coincident with Expression of Involucrin and Transglutaminase but Not Keratin-10; Journal of Virology; 1998; pp. 5016-5024; vol. 72 No. 6.
Vogel, T. U., et al., Multispecific Vaccine-Induced Mucosal Cytotoxic T Lymphocytes Reduce Acute-Phase Viral Replication but Fail in Long-Term Control of Simian Immunodeficiency Virus SIVmac239; Journal of Virology; 2003; pp. 13348-13360; vol. 77 No. 24.
Veazey, R. S., et al., Emergence and Kinetics of Simian Immunodeficiency Virus-Specific CD8 + T Cells in the Intestines of Macaques During Primary Infections; Journal of Virology; 2001; pp. 10515-10519; vol. 75 No. 21.

\* cited by examiner

1A

1B

1C

1D
pSIVmac239-EF1α/STR/IRES-GFP

SEQUENCE LISTING

```
<160> NUMBER OF SEQ ID NOS: 13

<210> SEQ ID NO 1
<211> LENGTH: 2482
<212> TYPE: DNA
<213> ORGANISM: Homo sapiens

<400> SEQUENCE: 1
aagcttctcc atgtgtcatg ggatatagct catccttatt atgttgggtg ggggttggac      60
agttacccag acttgtcatg tggacctgga gcttatgagg tcattcacat aggcagtgaa     120
agaacctctc ccatatacgt gaatgcctgt ctcccaaatg gggcaacctg tgggcagaat     180
aagggacttc tcagccctag aatgttgagg ttcccaac cctcccttg catacacaca         240 cacacaaaca ctccctcagc tgtatccact gccctctttc ccacaccta gctttgccca      300 gcagtcaaag gctcacacat accatcttct ccttaaggct cttattatgc cgtgagtcag     360
agggcgggag gcagatctgg cagatactga gccctgcta acccataaga ccggtgtgac      420
ttccttgatc tgagtctgct gccccagact gactgtcacg ggctgggaag aggcagattc     480
cccccagatg aagtcagcag cagagcacaa gggcatcagc gccaaagtaa ggatgcttga    540
ttagttcttc agggcagagt gggctgtgct tcctctgccc cagaaaatgg cacagtccct     600
gttctatggg aaaagaatg tgaggtccct gggtgggctc agggaacaga gaggtcatga     660
ggaggggata gcactgcaga aaccaagggt gccttgtgag tcctcctct gtcttttag      720 gcatgatcca ggaacatgac aaaattagtg ctttaaatag atttacttgg gctaagagaa     780
atgtgcctgt caggaaaact atggggaatc aggacacttc tcaaaattag ccccactgag    840
tattgtcttt ataattcctt ctttttggat tagattgtaa aaaagagagt gtaaatgaat     900
gatgtccata taataagtta ttagccaacc attaaaaaga aagggaagaa ataaatcagt     960
ttggttttta cacacacata cagacacaca catataaaca ttgatcaaca ctgaaatgtt    1020
taatagtcat tattttcggg tcgtaaaatt cactgttctt caatgaatac ttgtagagca    1080
catattatat gcagtagttt tgataggttc taggggtata gtggaaaaca taccaggtat    1140
```

```
acgctgctct tagcttattt tccagtggga aagatagaca ataagcaagt gaacaaatgc    1200
aaataaatta ctctagattg ttataagtga aattaagtac caatcccttta gatatggtac    1260 acagagaagg atctctgaca gaccccaaca ttgacactga agctgaaagg cataaaagaa    1320
ccagagacct ggggaggggc cggtgggcag aaggagagca ggtgccaagc ccccaggtgg    1380
agagctctgg gctcatctca ggaaccgaag ccctcagtg aggtaagaat atacctctca    1440
gggagagatt gacatgaatt ggggccccag aagaaggcag aagccaggta cccagggtct    1500
tttaaaccac ggcagtgagt ttgaatgtta tttcaagtgt gctggtgcac tgttggcacg    1560
ggggagagat gtgctcaaat ccccactctg aaagatttct taagctattt ctagagtatg    1620
atttacaaca ggaaatggat gatttgattc tgatctttat gccttcatgc atttaaaaaa    1680
gtacttaaga aagtagtttg gtttgtcatt ataaaaagca atacttattt ttatattgtg    1740
tagattcaat cttgtttcct tgcctagagt gggccgtgct ttggagttct tatgagcatg    1800
gcattcctga gaacttctct aactgcagcc tcgggcatag aggctgggca gcaagtggca    1860
gcagcagagg actcctagaa gccttctact tgactctact tggcctaaag tcaaactccc    1920
tccaccaaag acagagttta tttccacata ggatggagtt aaaaaatata ttctgagaga    1980
ggaagggctt gtggcccaag agaacacccc agaaatacca ccccttcatg ggaagtgact    2040
ctatcttcaa acatataacc cagcctggac atccccgaaa gacacataac tttccatttc    2100
atgcccttga agtgaatct tttggcctaa taatgagaac aaactcattt tgaaagtgga    2160
aaaattgaga ttcagagcag aagtttgact aaggtcacaa acagtagga tgcctcactc    2220 agctccctgt gcctaggtca gaaaagcatc acaggaatag ttgagctacc agaatcctct    2280
ggccaggcag gagctgtgtg tccctgggaa atggggccct aaagggtttg ctgcttaaga    2340
tgcctgtggt gagtcaggaa ggggttagag gaagttgacc aactagagtg gtgaaacctg    2400
tccatcacct tcaacctgga gggaggccag gctgcagaat gatataaaga gtgccctgac    2460
tcctgctcag tcgctctgcg ca                                              2482

<210> SEQ ID NO 2
<211> LENGTH: 461
<212> TYPE: DNA
<213> ORGANISM: Homo sapiens

<400> SEQUENCE: 2
gcctggcaca tagtaggccc tttaaaaatt tttttgggtc gggcgccatg gctcatgccc      60
gtaatcctaa cactttggga ggccaggtgg gcagatcact tgagtcagaa gttcgaaacc     120
agcctggtca acgtagtgaa accccatctc tactaaaaat acaaaaaatt tagccaggcg     180
tggtggcgca cgcctataat accagctact cgggaggctg aggcaggaga attgcttgaa     240
cccgggaggc agatgttgca gtgagccgag atcacgccac tgcactccag cctgggtgac     300
agagtgatac tacaccccc aaaaataaaa taaataaat aaatacaact ttttgagttg     360
ttagcaggtt tttcccaaat agggctttga agaaggtgaa tatagaccct gcccgatgcc     420
ggcggcctag gaagactttg tgatgccggc tggctaggaa g                         461

<210> SEQ ID NO 3
<211> LENGTH: 1292
<212> TYPE: DNA
<213> ORGANISM: Homo sapiens

<400> SEQUENCE: 3
```

```
tgattcactt caattcctga atctaactt ctgactttca agaaaattc cactttggca      60
gctgtacagg taccaacaac agtttaccct tacctggaag aagagccttg gaggagaaaa   120
cacaccatgt cggtatgggt gtgacaaagt ctacttttc tagcactcct ggggctcaca   180
gagaaggcat ttatcaaggg gcgagatgaa agcagactca gatttcatat agccagttct   240
tgcagtccat gtcagtaaaa gtgaaaaagc ccagcaataa tgcattgtct cattaaggct   300
aatgtgagta agataattca agtatgtaga tttctggtag tgtaattta tctcaacaaa   360
gaacttagaa caatgagaaa agtaaataga aaccataatc ctatcataac agcccctgaa   420
acctgtgagc gcaagggga tctagaatat ttccaatgcc cccttgcagt tagttaatcc    480
cctcccaaag gcactgttca gattcctcac cataggttag ttttccttat tctgcatttc   540
cctgactaat agtgttgtta agcacgtttt aatatgattt atatacatag aatcatacag   600
aacgtactct gctgtgttg gcttatttgc taaacatagt gtcttgatac acatcaaatt    660
cctgcttttt taatactttc ttaagttttc ttaatgctag gcagtatttc attgtatgaa   720
ttttccataa tttattgatt tacctgcaga tggacattta ggttattaca atttggggct   780
atatgaacaa agttgttacg aatatttatg tacaagtctt tcgtggacat gttatttctc   840
ttaaatgaat atttagggc agagcttctt ggtcatagca tggttgtatg tttaacttta    900
taagaaaccg ccaaattgtt ttctgcattg attgtgccac cttacattca tactagcact   960
gtatgagagt tccaggggct ccacctcctt gccacacttg ctttgtcatt aatttttaata  1020
ttagccattt tgtgggtct gaaatgatat cttatggggc ttttttaactg catttccctg   1080
actgataata tggttaagga tttcacatgc tttttggtca tttatacatt ttcacttgaa  1140
cataaatgta ggtctatttc tgagttcttt atgcttttca tttatctata tgtgtattca  1200
tacaccaaaa ccacacattc ttgattgatg agcatttata gtaagtattg aaaccagata  1260
gtgtgagacc tacaactttg ttattttcca ag                                1292

<210> SEQ ID NO 4
<211> LENGTH: 1220
<212> TYPE: DNA
<213> ORGANISM: Homo sapiens

<400> SEQUENCE: 4
atctcaacag cttgttctag aaattttta agcacagtat cacaaacagc actacataat      60
tgtaaaacat gtatgaatat acatccaa acaacagcaa tgtcatagcc tatgggtaga    120
tataatctta tacaatgtac caaaatccca atttacttca ctagacaaac tgttatacca   180
aattctgtac acagtatatc caagaaaatg tgttgttttt attgagaaac tgaacctagc   240
ttgggaacac atgtgcacag tctagttcat aatatttggt gcaagtatca ttctctaata   300
tagatttaca tttttgcaag caaatttta cttgcaatca taacatatcc aaattttccc   360
tttttactca atcagaactt agtgtaaagt actacaagtt agttcttcgg atttcatgct   420
aagaaaataa tgcagatttt ctgcattatt atggtcttca cagaaacctt aactatgatg   480
aatttaaaag tgcaaaataa tccaggataa ctttatgatt tcagattttt taatgttaaa   540
ataatgcca tcattaatta gaaaattcta aaatcattac ttccactttc ttaggcaaaa    600
tatcaatata ctctcatttg ccaaataaat taaaagatct cctacaaaca caatctccta   660
aattgtggtt ttatggcttt aatgtttat gtgtggcaac tattgatgct agttaaattt    720
ttagaaactt tttcttttg attccctaca gttgtctaca agaaccttat tgtagcatga    780
tcctgccaga cttatgcta tttgttgctc caattaaaac tgtttaaaac atgaatttga    840
```

```
aaaatcttat ttttaactata attttgtagc tgaaactttt ttttctaaac tttgcaaaca      900
ttctatgcaa cctgaattag tgctgagaaa aatggatctt aacggttgct caatgttctt      960
caacaggtga aaagcataat aaaacatgct catctgaact ccacccattt tcaatttcaa     1020
catagcaaac ctcctgttta ttcttagggc aaattcaaaa ttgtacatat taggattggt     1080
tattactgaa gataatttat gcaatcataa gccaagatg ctaagttggc aaaaagaaaa      1140
caatgtaagt aagcaaactc taacacatgt ggacacaccc tctcagtata taaaggcttg     1200
tcactgtcct tggtagcagg                                                1220

<210> SEQ ID NO 5
<211> LENGTH: 54
<212> TYPE: DNA
<213> ORGANISM: Artificial Sequence
<220> FEATURE:
<223> OTHER INFORMATION: HIV Primer

<400> SEQUENCE: 5
gcggccgctg cgcagaggca gaaagagcca ttggaggttc tctccagcac tagc           54

<210> SEQ ID NO 6
<211> LENGTH: 36
<212> TYPE: DNA
<213> ORGANISM: Artificial Sequence
<220> FEATURE:
<223> OTHER INFORMATION: HIV Primer

<400> SEQUENCE: 6
aggaggagca ttggtgttcc ctgctagact ctcacc                               36

<210> SEQ ID NO 7
<211> LENGTH: 21
<212> TYPE: DNA
<213> ORGANISM: Artificial Sequence
<220> FEATURE:
<223> OTHER INFORMATION: HIV Primer

<400> SEQUENCE: 7
gggccgggac agaaggctag a                                               21

<210> SEQ ID NO 8
<211> LENGTH: 21
<212> TYPE: DNA
<213> ORGANISM: Artificial Sequence
<220> FEATURE:
<223> OTHER INFORMATION: HIV Primer

<400> SEQUENCE: 8
gggccgggac agaaggctag a                                               21

<210> SEQ ID NO 9
<211> LENGTH: 21
<212> TYPE: DNA
<213> ORGANISM: Artificial Sequence
<220> FEATURE:
<223> OTHER INFORMATION: HIV Primer

<400> SEQUENCE: 9
cctctggggg agcagttggc a                                               21

<210> SEQ ID NO 10
<211> LENGTH: 22
<212> TYPE: DNA
```

```
<213> ORGANISM: Artificial Sequence
<220> FEATURE:
<223> OTHER INFORMATION: HIV Primer

<400> SEQUENCE: 10
gcatggtggg cagggataga gc                                              22

<210> SEQ ID NO 11
<211> LENGTH: 20
<212> TYPE: DNA
<213> ORGANISM: Artificial Sequence
<220> FEATURE:
<223> OTHER INFORMATION: HIV Primer

<400> SEQUENCE: 11
gctcaccggg tcccttccac                                                 20

<210> SEQ ID NO 12
<211> LENGTH: 20
<212> TYPE: DNA
<213> ORGANISM: Artificial Sequence
<220> FEATURE:
<223> OTHER INFORMATION: HIV Primer

<400> SEQUENCE: 12
acggcgacgt aaacggccac                                                 20

<210> SEQ ID NO 13
<211> LENGTH: 20
<212> TYPE: DNA
<213> ORGANISM: Artificial Sequence
<220> FEATURE:
<223> OTHER INFORMATION: HIV Primer

<400> SEQUENCE: 13
cggttcacca gggtgtcgcc                                                 20
```

INVOLUCRIN-DRIVEN RETROVIRAL EXPRESSION CASSETTES ENCODING HUMAN IMMUNODEFICIENCY VIRUS ENVELOPE GLYCOPROTEINS

REFERENCE TO RELATED APPLICATIONS

The present application relates to, claims the benefit of, and claims priority to U.S. Provisional Patent Application Ser. No. 61/632,431, filed Oct. 24, 2012, and U.S. Provisional Patent Application Ser. No. 61/793,658, filed Mar. 15, 2013, both of which are incorporated herein in their entireties.

STATEMENT OF GOVERNMENT SUPPORT

This invention was made with government support under Grant Numbers AI084171-01 and AI090705-01 awarded by National Institutes of Health. The government has certain rights in the invention.

FIELD OF INVENTION

The present invention relates to the field of differentiation-specific promoters and their use in the development of vaccines.

BACKGROUND OF THE INVENTION

Many viruses have developed strategies to either infect or traverse through the epithelial cells to establish infection in the host. Most of them are specific for a particular epithelium. For example, rotaviruses infect intestinal epithelial layers. Papillomaviruses chronically infect epidermal layers. About one-third of Human Papillomaviruses specifically infect the genital tract. Human respiratory syncytial virus (RSV) infects the superficial layer of the respiratory epithelium. Influenza viruses infect the pulmonary epithelial cells. While the Human Immunodeficiency Virus (HIV) infection is initiated primarily by affecting the epithelial cells in the oral, rectal or genital mucosa, the virus infects immune cells like macrophages or CD4+ T lymphocytes.

Significant strides in the development of HIV/AIDS vaccine candidates that are immunogenic in humans and non-human primates have been made. However, the goal of achieving protective immunity against HIV infection remains elusive. The nature of the HIV virus has created several barriers to effective immune control by the humoral and cellular forms of adaptive immunity. These barriers include the antigenic variability of the virus; its ability to generate antigen-escape variants; its inherent resistance to development of and targeting by neutralizing antibodies; down regulation of MHC class I and CD4 on infected cells; and, preferential destruction of viral-specific CD4+ T lymphocytes.

SUMMARY OF THE INVENTION

One of the main reasons for the failure of HIV vaccines is their inability to deliver antigens for prolonged periods of time, thus only producing a weak and transient protection at best. More than 90% of new HIV infections worldwide are transmitted by sexual intercourse, indicating that immunity should be directed to mucosal layers. Secondly, antigens should be provided permanently in order to maintain a pool of anti-HIV activated T cells. With the exception of attenuated viruses (which are not suitable for use in humans) no strategy has thus far led to the continuous release of antigen.

Transmission of HIV occurs predominantly across genital and rectal mucosal surfaces. The presence of HIV-specific T lymphocytes in the mucosa and at sites of early viral replication is likely to be an important factor for vaccine efficacy. An HIV/AIDS vaccine strategy would be to target HIV at the mucosal sites of transmission to prevent infection. The primary target cell for viral transmission via mucosal sites varies depending on the tissue. However, soon after crossing the mucosa, HIV rapidly spreads to the lymph nodes and other organs, where it replicates. So an effective vaccine would restrict viral replication at the mucosal portal of entry of the HIV virus. Most AIDS research using animals as models are conducted with the nonhuman primate model for AIDS infected with Simian Immunodeficiency Virus (SIV), a virus that is very similar to HIV and that causes AIDS-like disease. Of the vaccine approaches tested in the SIV/monkey model, vaccination with a live less-pathogenic/attenuated SIV has consistently yielded the most effective and most durable protection against infection with pathogenic SIV. However, safety issues preclude the use of live attenuated SIV vaccines in humans. Thus, vaccine strategies need to be developed to combine both safety and protection. One approach is the use of a SIV that cannot replicate and that is limited to a single cycle of infection.

An embodiment of the current invention is a vaccine that will be delivered to epithelial stem cells at the basal layer of the epithelium. This vaccine will have a promoter specific to terminally differentiated epithelial cells and a gene of interest. This promoter will drive the expression of proteins of interest leading to protein production in the upper parts of the epithelial layer. The protein of interest expressed by the epithelial cells will function as antigens. Thus, the epithelial stem cells will continuously release new antigen producing cells without being eliminated by the immune response. An embodiment of the invention is a single dose, life-long lasting vaccine. In another embodiment, the vaccine could be adapted to other pathogenic infections requiring participation from both cellular and humoral immunity mechanisms.

Certain embodiments of the current invention provide two features, namely: 1) a prolonged stimulation of the immune system with viral antigens, which can provide a strong barrier to viral replication; and, 2) a targeted immune response at the site of primary replication of the virus.

One embodiment of the invention is a nucleic acid composition containing an expression cassette that contains a differentiation-specific transcriptional regulatory element and a viral gene of interest. Another embodiment of the invention is a nucleic acid composition containing an expression cassette that then contains an involucrin promoter and an HIV envelope protein. Certain embodiments of the invention include the involucrin promoter as described by SEQ ID NO: 001. Other embodiments may include nucleic acid compositions that contain biologically functional equivalents of the involucrin promoter.

One embodiment of the invention is a nucleic acid composition containing an expression cassette containing a differentiation-specific transcriptional regulatory element, and where the differentiation-specific transcriptional regulatory element is selected from a group consisting of a blood cell-specific transcriptional regulatory element, a stratum-specific transcriptional regulatory element, a pathological state-specific transcriptional regulatory element, and combinations thereof.

Another embodiment of the invention is a nucleic acid composition wherein the differentiation-specific transcriptional regulatory element is a blood cell-specific transcriptional regulatory element. Another embodiment of the invention is a nucleic acid composition wherein the differentiation-specific transcriptional regulatory element is a stratum-specific transcriptional regulatory element.

An embodiment of the invention is a nucleic acid composition wherein the differentiation-specific transcriptional regulatory element is a transcriptional regulatory element of an involucrin gene. Another embodiment of the invention is a nucleic acid composition containing a gene of interest that encodes a viral protein.

An embodiment of the invention is a nucleic acid composition containing a gene of interest that encodes a viral protein derived from a retrovirus.

Another embodiment of the invention is a nucleic acid composition containing a gene of interest that encodes a viral protein derived from a lentivirus.

Another embodiment of the invention is a nucleic acid composition containing a gene of interest that encodes a viral protein derived from a human immunodeficiency virus.

Another embodiment of the invention is a nucleic acid composition containing a gene of interest that encodes a viral protein derived from a simian immunodeficiency virus.

An embodiment of the invention is a nucleic acid composition as part of an immunogenic composition for eliciting an immune response in a subject. Such immunogenic compositions may further contain an effective amount of a pharmaceutically acceptable vehicle.

An embodiment of the invention is a method of delivering a nucleic acid composition containing a gene of interest under the control of a differentiation-specific promoter to a subject by administering to a subject such nucleic acid composition.

Another embodiment of the invention is a method of administering the nucleic acid composition to a stem cell of an epithelial layer in the subject.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

FIG. 1A is a representation of the full-length SIVmac239 genome and encoding regions. FIG. 1B is a representation of 3'-half of SIVmac239 (p239SpE3') and of 5'-half of SIVmac239 (p239SpSp5') plasmids used as starting material to set up the different constructs. FIG. 1C is a representation of SIVmac239-STR and SIVmac239-EF1a/STR plasmids, lacking portions of the 5'U3 regions in both LTR. FIG. 1D is a representation of SIVmac239-EF1a/STR/IRES-GFP plasmid where nef gene has been deleted by insertion of an IRES-GFP region between positions 9500 and 9690 in SIVmac239-EF1a/STRconstruct.

FIGS. 3A-3D show the expression of green fluorescent protein when the GFP gene is under the control of the involucrin minimal promoter. FIG. 3A is the vector drawings corresponding to the GFP encoding region under the transcriptional control of the involucrin minimal promoter (pRRL.SIN.cPPT.pINV-GFP.WPRE). FIG. 3B is an illustration of the skin layers. FIG. 3C is a contrast microscopic view of the region of interest, i.e., sample of mouse epithelium inoculated with pINV-GFP construct and FIG. 3D is the fluorescence microscopic view of the same region shown in FIG. 3C.

FIGS. 10A-10D show the expression of the SIV-HIV constructs in normal human epidermal keratinocytes (NHEK). FIG. 10A examines the expression of keratin-6 that confirms the keratinocyte nature of the NHEK cells, FIG. 10B shows the fluorescence and light microscopic images of control cells (left panel, top and bottom), and NHEK cells transfected with involucrin promoter driven HIV construct (noted HIVpInv, right panel, top and bottom). FIG. 10C first shows fluorescence and light microscopic images of control cells in the absence of calcium (left panel, top and bottom), and NHEK cells transfected with involucrin promoter driven SIV construct also in the absence of calcium (noted SIVpInv, middle and right panels, top and bottom). FIG. 10C also shows fluorescence and light microscopic images of control cells in the presence of calcium (left panel, top and bottom), and NHEK cells transfected with involucrin promoter driven SIV construct also in the presence of calcium (noted SIVpInv, middle and right panels, top and bottom). FIG. 10D is a flow cytometry analysis of the cells and their expression of the green fluorescent protein in the presence and absence of calcium in the culture media.

DETAILED DESCRIPTION OF THE INVENTION

Figure 1:
FIGS. 1A-1D are schematic representations of the nucleic acid compositions used to construct the recombinant SIV nucleic acid composition.
Figure 1:
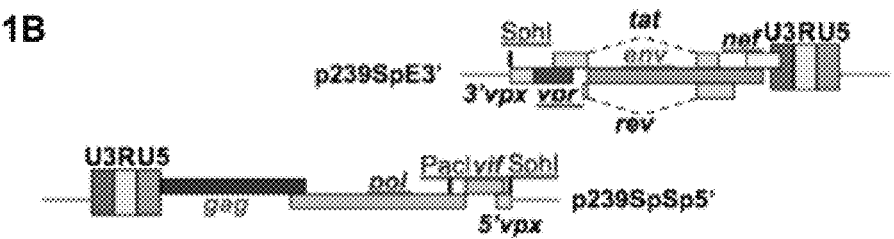
Figure 1:
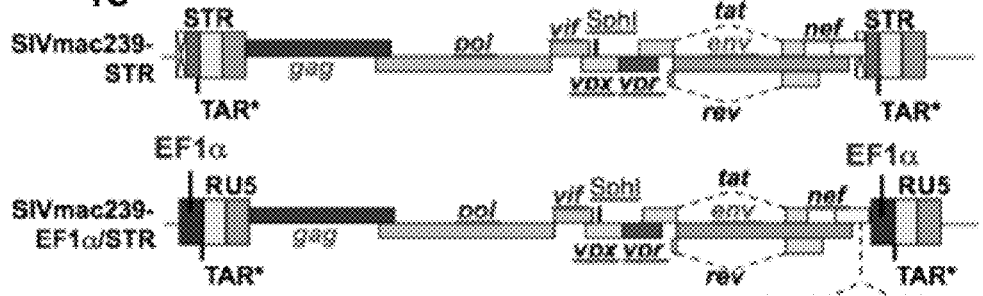
Figure 1:
Figure 1:
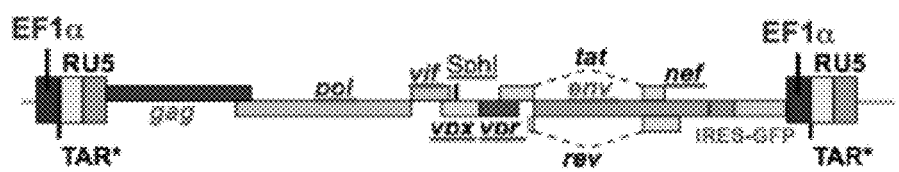

Before describing the embodiments of the present invention in detail, several terms used in the context of embodiments of the present invention will be defined. In addition to these terms, others are defined elsewhere in the specification, as necessary. Unless otherwise expressly defined herein, terms of art used in this specification will have their art-recognized meanings.

To more readily facilitate an understanding of the invention, the meanings of terms used herein will become apparent from the context of this specification in view of common usage of various terms and the explicit definitions provided below.

As used herein, the terms "comprising," "containing," "including," and "such as" are used in their open, non-limiting sense.

A "nucleic acid" or a "nucleic acid composition" means any deoxyribonucleotide or ribonucleotide polymer in either single-stranded or double-stranded forms. A nucleic acid composition may exist as a single polynucleotide or as two or more separate polynucleotides. Unless otherwise indicated, a nucleic acid composition includes known analogues of natural nucleotides that function in manner similar to naturally occurring nucleotides. Unless otherwise indicated, a particular nucleic acid sequence includes the complementary sequence thereof. For example, without limitation, a nucleic acid composition may be a vector, a plasmid, phagemid, or a cosmid, or it may be capable of stable integration into the host cell genome. A nucleic acid composition may be capable of replication in eukaryotic cells or prokaryotic cells or both. It may be present as a single copy or in multiple copies inside a cell. Examples of useful nucleic acid compositions that can be modified for use in the present invention include, but are not limited to, the pSP72 plasmid or pRRLSIN.cPPT.PGK-GFP.WPRE, SIVmac239 construct, p239SpE3' construct, p239SpSp5' construct, SIVmac239-STR construct, SIVmac239 EF1alpha/STR construct, pSIVmac239-EF1alpha/STR/IRES-GFP construct, pINV/SIV/deltaNef/IRES-GFP and pCMV-IE/SIV/deltaNef/IRES-GFP replicative-efficient constructs, and pINV/SIVrep-def and pCMV-IE/SIVrep-def constructs. An embodiment may include one or more genes inserted into an expression vector, in proper orientation and in proximity to a promoter such that under proper conditions, expression of the polynucleotide of choice can be directed in an appropriate host cell. A nucleic acid composition may comprise at least one origin of replication and may also comprise a gene for a marker by which it can be identified or selected when inserted into a host cell. Useful markers are well known in the art and include for example, without limitations, markers that confer resistance to antibiotics, colorigenic or fluorogenic properties. The choice of a nucleic acid composition will depend on what host cell will be used and what properties are desired of the polynucleotide of choice.

"Packaging systems" mean a set of viral constructs containing genes that encode viral proteins involved in packaging a nucleic acid composition, and a packaging cell line. The enzymatic machinery present in the packaging cell line is engineered to produce a desired level of the nucleic acid composition of interest and ail the structural proteins required for producing viral or pseudoviral particles. This system has notably been used for lentiviruses where it comprises Gag and Env genes along with Pol genes. The latter gene ensures RNA retrotranscription and integration into the host cell genome. Packaging systems can also expand the tissue tropism of the nucleic acid compositions. For example, packaging systems produced pseudotyped viral particles containing a lentiviral genome and the surface glycoprotein from vesicular stomatitis virus (VSV-G). VSV is been commonly used for producing pseudotyped particles because it is highly-stable and confers a wide host tissue range, because of the binding of VSV-G to a cell surface lipid.

"Replication defective" means the available genetic information in the nucleic acid composition, for example a recombinant virus particle, does not permit the autonomous replication of the nucleic acid composition under consideration in a host cell. So any reproduction of viral particles requires the supplementation of replication machinery by components of the host cell or by components supplied by other nucleic acid compositions present in the host cell by infection or transfection.

A "transcriptional regulatory element" means a nucleotide sequence that acts in cis to activate, decrease and regulate the transcription and the level of transcription of an operatively linked polydeoxyribonucleotide. In one embodiment, a transcriptional regulatory element regulates the level of translation of a polyribonucleotide by favoring the presence of a polyribonucleotide in a media (transcripts) that is used as a template for translation machinery to generate polymers of amino acids (proteins). An expression regulatory sequence can be a promoter, enhancer, silencer, insulator, transcription terminator, start codon (ATG), splicing signal for intron excision and maintenance of the correct reading frame, the stop codon, ribosome binding site such as an internal ribosome entry site, or the like.

A transcriptional regulatory element can be a constitutively active regulatory element or can be an inducible regulatory element, including an inducible regulatory element that is inactive in the absence of an inducing agent, or an element that is active at a basal level and is induced to a higher level in the presence of the inducing agent. In addition, the transcriptional regulatory element can be a tissue-specific regulatory element, which is active in only one or a few specific cell types, or can be a developmental stage specific regulatory element.

A "differentiation-specific transcriptional regulatory element" means a transcriptional regulatory element, which is active only during a certain stage of differentiation. This active state is function of the presence of DNA binding transcription factors (activating or inhibiting transcription factors) that bind to the regulatory element (promoter, enhancer, and/or silencer). The expression of transcription factors in the cells is function of the cell cycle state and the level of maturation of the cell. Thus the transcriptional regulation of a given transcriptional unit is function of the level of expression of transcription factors in the cells that are themselves function of the stage of differentiation of the cell. For example, a differentiation-specific transcriptional regulatory element may be active only in the mature cells of hematopoietic cells (including, but not limited to, Ig promoter, CD4 promoter, CD8 promoter, CD11c promoter, CD80 promoter, CD86 promoter, MHC-I promoter, MHC-II promoter). Another example, a differentiation-specific transcriptional regulatory element may be active only in the mature cells of the epithelial layer (including, but not limited to, Involucrin, Matrix metalloproteinase-9, Keratin-10, Loricrin). The importance of the transcription factor-binding site for AP-1 transcription factor in the Involucrin promoter to induce the expression of the Involucrin in corneal epithelium in vivo is known. The induction of Matrix metalloproteinase-9 in normal human bronchial epithelial cells is by the TNF-alpha via NF-kappaB-mediated pathway. It has also been shown that AP-1 transcription factor expression in wounded fetal skin induces expression of both Keratin-10 and loricrin as differentiation markers for re-epithelialization in wounded areas. Another example of a differentiation-specific transcriptional regulatory element may be one that is active only when the cell is in a pathologic state, like when a cell becomes cancerous or when it metastasizes. In another example, the differentiation-specific transcriptional regulatory element may be selected from a group consisting of a blood cell-specific transcriptional regulatory element, a stratum-specific transcriptional regulatory element, a pathological state-specific transcriptional regulatory element, and combinations thereof. Using a combination of promoters facilitates the use of the nucleic acid compositions in two different cell populations. For example, a viral packaging unit could contain nucleic acid compositions that contain viral genes under the control of both a stratum-specific transcriptional regulatory element and a blood cell-specific transcriptional regulatory element. The stratum-specific transcriptional regulatory element would modulate the expression of the viral genes during epithelial cell differentiation. If the blood cells also acquired the viral units, then the blood cell-specific transcriptional regulatory element would modulate the expression of the viral genes during the blood cell differentiation process.

An "epithelial layer" means either an external or an internal epithelial surface of the body. Epithelial tissues line the cavities and surfaces of structures throughout the body, and also form many glands. Functions of epithelial cells include secretion, selective absorption, protection, transcellular transport and detection of sensation. Epithelial layers are avascular. For example, without limitations, an epithelial layer includes the mucosal lining of viscera and body cavities, like the cervix, vagina, rectum, or the oral cavity, and digestive or urinary tract epithelia. Epithelial tissue that is only one cell thick is known as simple epithelium. There are three principal morphologies associated with epithelial cells. Squamous epithelium has cells, which are wider than they are tall (flat and scale-like). Cuboidal epithelium has cells whose height and width are approximately the same (cube shaped). Columnar epithelium has cells taller than they are wide (column shaped). In addition, the morphology of the cells in transitional epithelium may vary from squamous to cuboidal, depending on the amount of tension on the epithelium. If the epithelial layer is two or more cells thick, it is known as stratified epithelium. However, when taller simple epithelial cells (columnar) are viewed in cross section with several nuclei appearing at different heights, they can be confused with stratified epithelia. This kind of epithelium is therefore described as "pseudo stratified" epithelium. All stratified squamous epithelia such as vaginal or oral epithelium present the same pattern of differentiation differing chiefly in the number of epithelial layers, degree of keratinization, and mucous production.

In an embodiment of the invention, epithelial stem cells are used as a permanent source of viral antigen and their differentiated offspring as antigen-producing presenting cells, which would also stimulate dendritic cells via cross priming. Using the SIV single cycle (SIVsc) approach, which has been shown to be a very safe strategy compared to traditional attenuated lentivirus vaccines, the SIVsc genome has been cloned under the control of the Involucrin promoter. This vaccine is then administered to target epithelial stem cells from different tissues (epidermal, vaginal, rectal). Basal layer cells divide and differentiate thus triggering SIV antigen expression and direct and cross priming. Embodiments of the invention include vaccines containing the involucrin promoter as described by SEQ ID NO: 001. Other embodiments include vaccines that contain biologically functional equivalents of the involucrin promoter.

A "promoter" means a polynucleotide sequence in a nucleic acid composition that controls transcription of a gene of interest to which it is operably linked. A promoter may be present on the same nucleic acid composition as the gene of interest under its control (cis-activation), but also that can control transcription of the gene of interest on another nucleic acid composition in trans. A promoter may include signals for RNA polymerase binding and transcription initiation. The promoters used will be functional in the cell type of the host cell in which expression of the selected sequence is contemplated. A promoter is usually located upstream of an expression cassette with the direction of transcription equivalent to the desired direction of translation of the polypeptide (cis-activation), but can also be located 1) downstream of the transcriptional cassette/cluster; and, 2) in another locus of the genome (trans-activation). A promoter is typically a sequence or sequences with affinity for transcription factors and an RNA polymerase sufficient to induce binding that is required for transcriptional initiation.

Examples of Promoters:

```
Involucrin promoter:
                                                     SEQ ID NO: 001
aagcttctccatgtgtcatgggatatagctcatccttattatgttgggtgggggttggacagttacccagac ttgtcatgtggacctggagcttatgaggtcattcacataggcagtgaaagaacctctcccatatacgtaat gcctgtctcccaaatggggcaacctgtgggcagaataagggacttctcagccctagaatgttgaggtttccc caaccccctccttgcatacacacacacacaaacactccctcagctgtatccactgccctctttcccacaccc tagctttgcccagcagtcaaaggctcacacataccatcttctccttaaggctcttattatgccgtgagtcag agggcgggaggcagatctggcagatactgagccctgctaacccataagaccggtgtgacttccttgatctg agtctgctgccccagactgactgtcacgggctgggaagaggcagattccccccagatgaagtcagcagcaga gcacaagggcatcagcgccaaagtaaggatgcttgattagttcttcagggcagagtgggctgtgcttcctct gccccagaaaatggcacagtccctgttctatgggaaaaagaatgtgaggtccctgggtgggctcagggaaca
```

-continued

```
gagaggtcatgaggaggggatagcactgcagaaaccaagggtgccttgtgagtcctccctctgtcttttag gcatgatccaggaacatgacaaaattagtgctttaaatagatttacttgggctaagagaaatgtgcctgtca ggaaaactatggggaatcaggacacttctcaaaattagccccactgagtattgtctttataattccttcttt ttggattagattgtaaaaagagagtgtaaatgaatgatgtccatataataagttattagccaaccattaaa aagaaagggaagaaataaatcagtttggttttttacacacacatacagacacacacatataaacattgatcaa cactgaaatgtttaatagtcattattttcgggtcgtaaaattcactgttcttcaatgaatacttgtagagca catattatgcagtagttttgataggttctaggggtatagtggaaaacataccaggtatacgctgctctta gcttattttccagtgggaaagatagacaataagcaagtgaacaaatgcaaataaattactctagattgttat aagtgaaattaagtaccaatcctttagatatggtacacagagaaggatctctgacagaccccaacattgaca ctgaagctgaaaggcataaaagaaccagagacctggggaggggccggtgggcagaaggagagcaggtgccaa gcccccaggtggagagctctgggctcatctcaggaaccgaaggccctcagtgaggtaagaatatacctctca gggagagattgacatgaattgggccccagaagaaggcagaagccaggtacccagggtctttaaaccacgg cagtgagtttgaatgttatttcaagtgtgctggtgcactgttggcacggggagagatgtgctcaaatcccc actctgaaagatttcttaagctatttctagagtatgatttacaacaggaaatggatgatttgattctgatct ttatgccttcatgcatttaaaaaagtacttaagaaagtagtttggtttgtcattataaaaagcaatacttat ttttatattgtgtagattcaatcttgtttccttgcctagagtgggccgtgctttggagttcttatgagcatg gcattcctgagaacttctctaactgcagcctcgggcatagaggctgggcagcaagtggcagcagcagaggac tcctagaagccttctacttgactctacttggcctaaagtcaaactccctccaccaaagacagagtttatttc cacataggatggagttaaaaaatatattctgagagaggaagggcttgtggcccaagagaacaccccagaaat accaccccttcatgggaagtgactctatcttcaaacatataaccccagcctggacatcccgaaagacacata actttccatttcatgcccttgaaagtgaatcttttggcctaataatgagaacaaactcattttgaaagtgga aaaattgagattcagagcagaagtttgactaaggtcacaaaacagtaggatgcctcactcagctccctgtgc ctaggtcagaaaagcatcacaggaatagttgagctaccagaatcctctggccaggcaggagctgtgtgtccc tgggaaatgggccctaaagggtttgctgcttaagatgcctgtggtgagtcaggaagggggttagaggaagtt gaccaactagagtggtgaaacctgtccatcaccttcaacctggagggaggccaggctgcagaatgatataaa gagtgccctgactcctgctcagtcgctctgcgca
```

Matrix metalloproteinase-9 promoter (MMP-9):

SEQ ID NO: 002

```
gcctggcaca tagtaggccc ttaaaaatt ttttgggtc gggcgccatg gctcatgccc gtaatcctaa cactttggga ggccaggtgg gcagatcact tgagtcagaa gttcaaaacc aacctggtca acgtaatgaa accccatctc tactaaaaat acaaaaaatt tagccaggcg tggtggcgca cgcctataat accagctact cgggaggctg aggcaggaga attgcttgaa cccgggaggc agatgttgca gtgagccgag atcacgccac tgcactccag cctgggtgaca gagtgatac tacaccccc aaaaataaaa taaataaat aaatacaact ttttgagttg ttagcaggtt tttcccaaat agggctttga agaaggtgaa tatagaccct gcccgatgcc gacggcctaa aagactttg tgataccggc tggctaggaa g
```

Loricrin promoter:

SEQ ID NO: 003

```
tgattcactt caattcctaa aatctaactt ctgactttca aagaaaattc cactttggca gctgtacagg taccaacaac agtttacccct tacctggaag aagagccttg gaggagaaaa cacaccatgt cggtatgggt gtgacaaagt ctacttttttc tagcactcct ggggctcaca gagaaggcat ttatcaaggg gcgagatgaa agcagactca gatttcatat
```

-continued agccagttcttgcagtccat gtcagtaaaa gtgaaaaagc ccagcaataa tgcattgtct cattaaggctaatgtgagta agataattca agtatgtaga tttctggtag tgtaatttta tctcaacaaagaacttagaa caatgagaaa agtaaataga aaccataatc ctatcataac agccctgaaacctgtgagc gcaaggggga tctagaatat ttccaatgcc cccttgcagt tagttaatccctcccaaag gcactgttca gattcctcac cataggttag tttttcctat tctgcatttccctgactaat agtgttgtta agcacgtttt aatatgattt atatacatag aatcatacagaacgtactct gctgtgtttg gcttatttgc taaacatagt gtcttgatac acatcaaattcctgctttt taatactttc ttaagttttc ttaatgctag gcagtatttc attgtatgaattttccataa tttattgatt tacctgcaga tggacattta ggttattaca atttggggctatatgaacaa agttgttacg aatatttatg tacaagtctt tcgtggacat gttatttctcttaaatgaat atttaggggc agagcttctt ggtcatagca tggttgtatg tttaactttataagaaaccg ccaaattgtt ttctgcattg attgtgccac cttacattca tactagcactgtatgagagt tccaggggct ccacctcctt gccacacttg ctttgtcatt aattttaatattagccattt tgtgggtct gaaatgatat cttatgggc tttttaactg catttccctgactgataata tggttaagga tttcacatgc ttttggtca tttatacatt ttcacttgaacataaatgta ggtctatttc tgagttcttt atgcttttca tttatctata tgtgtattcataccaaaa ccacacattc ttgattgatg agcatttata gtaagtattg aaaccagatagtgtgagacc tacaactttg ttattttcca ag Keratin-10 promoter:

SEQ ID NO: 004 atctcaacag cttgttctag aaattttaa agcacagtat cacaaacagc actacataattgtaaaacat gtatgaatat atacatccaa acaacagcaa tgtcatagcc tatgggtagatataatctta tacaatgtac caaaatccca atttacttca ctagacaaac tgttataccaaattctgtac acagtatatc caagaaaatg tgttgttttt attgagaaac tgaacctagcttgggaacac atgtgcacag tctagttcat aatatttggt gcaagtatca ttctctaatatagatttaca ttttttgcaag caaatttta cttgcaatca taacatatcc aaattttccctttttactca atcagaactt agtgtaaagt actacaagtt agttcttcgg atttcatgctaagaaaataa tgcagatttt ctgcattatt atggtcttca cagaaaacctt aactatgatgaatttaaaag tgcaaaataa tccaggataa ctttatgatt tcagatttt taatgttaaaaataatgcca tcattaatta gaaaattcta aaatcattac ttccactttc ttaggcaaaatatcaatata ctctcatttg ccaaataaat taaaagatct cctacaaaca caatctcctaaattgtggtt ttatggcttt aatgttttat gtgtggcaac tattgatgct agttaaatttttagaaactt tttcttttg attccctaca gttgtctaca agaaccttat tgtagcatgatcctgccaga ctttatgcta tttgttgctc caattaaaac tgtttaaaac atgaatttgaaaaatcttat tttaactata attttgtagc tgaaactttt ttttctaaac tttgcaaacattctatgcaa cctgaattag tgctgagaaa aatggatctt aacggttgct caatgttcttcaacaggtga aaagcataat aaaacatgct catctgaact ccacccattt tcaatttcaacatagcaaac ctcctgttta ttcttagggc aaattcaaaa ttgtacatat taggattggttattactgaa gataatttat gcaatcataa gccaaagatg ctaagttggc aaaaagaaaacaatgtaagt aagcaaactc taacacatgt ggacacaccc tctcagtata taaaggcttgtcactgtcct tggtagcagg The term "a sequence essentially as set forth in SEQ ID NO: 001" means that the sequence substantially corresponds to a portion of SEQ ID NO: 001 and has relatively few nucleotides that are not identical to, or a biologically functional equivalent of, the nucleotides of SEQ ID NO: 001. Generally, when a nucleic acid composition contains a sequence essentially as set forth in a particular SEQ ID, it means that the sequence substantially corresponds to a portion of that particular SEQ ID and has relatively few nucleotides that are not identical to, or a biologically functional equivalent of, the nucleotides of that SEQ ID. It is further contemplated that nucleic acid compositions may contain a polynucleotide that has a stretch of contiguous nucleotides from a particular SEQ ID; for example, lengths of 10, 20, 50, 75, 100, 125, 150, 200, 250, 500, 1000, as well as the entire lengths of the SEQ ID, may be considered appropriate for use in certain embodiments of the invention.

The term "biologically functional equivalent" is well understood in the art and is further defined in detail herein. Accordingly, allowing for the degeneracy of the genetic code, sequences that have about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, about 70% to about 80%, and more preferably about 81% and about 90%; or even more preferably, between about 91% and about 99%; of nucleotides that are identical or functionally equivalent to the nucleotides of any of the SEQ IDs described herein will be biologically functional equivalents of the SEQ ID, provided the biological activity of the nucleotide sequence is maintained. In certain other embodiments, the invention concerns isolated DNA segments and nucleic acid compositions that include within their sequence a nucleic acid sequence essentially as set forth in SEQ ID NO: 001. Further embodiments may include nucleic acid compositions that contain biologically functional equivalents of the involucrin promoter.

An "expression cassette" means a polynucleotide construct that contains coding sequences for one or more proteins that may be operably linked to a promoter sequence. An expression cassette may comprise other transcriptional regulatory sequences to direct proper transcription of the coding sequence into RNA. The spacing and organization of these regulatory sequences are flexible, so that the promoter function is preserved when the regulatory sequences are inverted or moved relative to one another. An expression cassette may also comprise any of a variety of translation regulatory sequences that may be necessary or desired to direct proper translation of the RNA in the intended host cell. The expression cassette is part of a nucleic acid composition and contains at least one gene that can be expressed by the host cell. The expression cassette may include other regulatory sequences including, but are not limited to, an initiation codon for translation start, a termination codon for ending translation, an RNA splice site, a transcriptional termination site, and a polyadenylation site. The expression cassette may contain the gene sequence for a protein of interest. An expression cassette may contain coding sequences for a tag or a post-translational modification site. An expression cassette may include an origin of replication or chromosome integration elements. In particular, it may contain sequences that are homologous to the host-cell genome in order to force a site-specific integration by homologous recombination.

A nucleotide composition or a sequence "encoding" a polypeptide or a gene means a nucleotide sequence that, when transcribed and/or expressed, results in the production of an RNA, polypeptide or protein. The nucleotide sequence "encodes" that RNA or it encodes the amino acid sequence for that polypeptide or protein. The nucleic acid compositions may contain an element(s) that permits stable integration of the nucleic acid, or of a smaller part of the nucleic acid, into the host cell genome or autonomous replication of the nucleic acid composition independent of the genome of the cell.

The vectors, or smaller parts of the vectors such as amplification units of the present invention, may be integrated into the host cell genome when introduced into a host cell. For chromosomal integration; the vector may rely on the nucleic acid sequence encoding the polypeptide or any other element of the vector for stable integration of the vector into the genome by homologous or nonhomologous recombination.

"Operably linked," when referring to DNA segments, indicates that the segments are arranged so that they function in concert for their intended purposes, e.g., transcription initiates in the promoter and proceeds through the coding segment to the terminator.

The term "gene of interest" means nucleotides encoding any type of self or non-self polypeptide or protein of interest. Genes of interest in the present embodiment include proteins that are capable of eliciting an immune response, like viral and bacterial antigens. Interleukins like IL-2 or IL-12 may also be part of the nucleic acid compositions.

The term "viral gene of interest" means nucleotides encoding a polypeptide of interest that comprises all or a part of one or more viral proteins. Examples include, but are not limited to, HIV-derived structural (Gag, Pol, Env) or non-structural antigens (nef, rev, vpu, vpx, tat, vif antigen) in the case of HIV or SIV or SHIV.

The term "polypeptide of interest" means an isolated or synthetic full length protein, an isolated or synthetic full length polypeptide, or an isolated or synthetic full length oligopeptide. The terms polypeptide of interest or protein of interest may be used interchangeably. A protein, polypeptide or oligopeptide has a minimum size of two amino acids. Examples of recombinant polypeptides that can be used in the present invention include polypeptides derived from prokaryotic and eukaryotic organisms. Such organisms include phages, viruses, bacteria, fungi, plant or animals. Types of polypeptides that can be utilized in the present invention include, without limitations, enzymes, structural proteins, membrane proteins, transport proteins, and other peptides or proteins capable of eliciting an immune response. The polypeptide of interest may be expressed as part of an expression cassette. The coding sequence can be a native coding sequence for the polypeptide of interest or may be a coding sequence that has been selected, improved, or optimized for use in the host cell. The polypeptide of interest may be a single protein or a group of proteins like all that is required to form a virus, such as epitopes, full capsid proteins, or full proteins of interest.

A "host cell" or "cell" means any cell of any organism that is selected, modified, transformed, grown or used or manipulated in any way for the production of a substance by the cell. For example, a host cell may be one that is manipulated to express a particular gene of interest, a DNA or RNA sequence, a protein of interest, like an antigen. Host cells can further be used for screening or other assays to detect the presence of the particular biological product. Host cells may be cultured in vitro or as one or more cells in a non-human animal (e.g., a transgenic animal or a transiently transfected animal). Nucleic acid compositions according to the invention can be introduced into the target host cells by various methods known to one skilled in the art.

Nucleic acid compositions according to the invention can be delivered to a subject by various methods known to one skilled in the art. The subject is typically a mammal, such as a human, a monkey or an ape. The nucleic acid compositions may be delivered to a subject through intravenous, mucosal, intramuscular, or subcutaneous delivery. The nucleic acid compositions may be incorporated in a variety of delivery vectors, including but not limited to attenuated or live organisms like a bacterium or a virus, or a liposome carrier. Examples of viral delivery vectors include, but are not limited to, human papilloma viruses, adenoviruses, retroviruses (including lentiviruses), adeno-associated viruses, and herpes simplex virus type 1. Viral delivery vectors may be produced by packaging systems that do not form new virus in the host cell, but simply act as carriers for the nucleic acid compositions of interest. Physical methods of delivery include, but are not limited to, taking nucleic acid compositions and forcing them into cells through such means as electroporation, sonoporation, or particle bombardment. Chemical methods of delivery include, but are not limited to, lipids, polymers, or proteins that may complex with the nucleic acid composition of the invention, condensing it into particles and directing it to the cells. The delivery vehicles may comprise molecules that target the nucleic acid composition to a particular cell or tissue in a subject. The nucleic acid compositions may be delivered as immunogenic compositions.

An "immunogenic composition" means a composition, which contains elements having the capacity to elicit, in vivo or in vitro, a cellular and/or humoral type immune response. An immunogenic composition may stimulate the production of B lymphocytes that produce antibodies to block the virus from infecting healthy cells. An immunogenic composition may maintain the memory T lymphocyte response. In one embodiment, an immunogenic composition is a vaccine. A vaccine is an immunogenic composition that elicits the subject's own immune system to seek out and destroy an infecting agent before it causes a pathological response in the subject. A vaccine may function as a therapeutic vaccine or a preventive vaccine. Therapeutic vaccines control infection in patients who are already positive for the pathogen. Preventive vaccines prevent the subjects from becoming infected with the pathogen. Vaccines may be either live, but attenuated, infectious agents (virus or bacteria) or an inactivated or killed form of the agent. A vaccine consisting of a live bacteria or virus must be non-pathogenic. A bacterial or viral culture is attenuated (weakened) by physical or chemical treatment. Although the agent is non-virulent, it can still elicit an immune response in a subject treated with the vaccine.

In one embodiment, an immunogenic composition contains a pharmaceutically acceptable vehicle and a nucleic acid composition containing a viral gene of interest. The immunogenic compositions may be in any solid or liquid or gaseous form or some combinations thereof, which is normal for pharmaceutical administration, including but not limited to a gel, a pressurized suspension, microemulsions, aerosolized formulations, any support that allows for controlled release, or a nanoparticle. A pharmaceutically acceptable vehicle may contain a physiologically acceptable carrier that is non-toxic to the treated subject and is compatible with the nucleic acid composition. Suitable pharmaceutical carriers include liquid carriers, such as normal saline and other non-toxic salts at or near physiological concentrations. The pharmaceutically acceptable vehicle may also comprise components which increase or are capable of increasing the immunogenicity of the nucleic acid compositions described in the invention, in particular, other immunogenic nucleotides, peptides, specific or non-specific immunity adjuvants such as alum, Freund's adjuvant, polysaccharides or equivalent compounds. Components of an immunogenic composition may be administered sequentially or contemporaneously. For example, without limitations, the nucleic acid composition containing a viral gene of interest may be administered before or after the subject is treated with a pharmaceutically acceptable vehicle containing an immune modulator.

A person versed in the art will be able to prepare immunogenic compositions of the nucleic acid composition and to determine, as a function of several factors, the preferred mode of administration and the amount, which has to be administered. Factors which may influence the choice include: the nature of the treatment, the exact nature of the ingredients, active or non active, components in the composition, the stage of the disease, the condition, age and weight of the patient, and other factors.

In one embodiment of the invention, a novel nucleic acid composition was developed to function as an immunogenic composition based on the ability of lentiviral vectors integrated in epidermal or mucosal epithelial stem cells to induce virus-specific cellular immune responses at mucosal sites against HIV/SIV. Keratinocytes in the proliferative basal cell layer up regulate transcription of cornified envelope precursor proteins such as involucrin, loricrin, filaggrin, and proteinases such as matrix metalloproteinase-9, and switch their keratin expression from keratin type 5/keratin type 14 (K5/K14) to K1/K10 as they differentiate and move upward. AH stratified squamous epithelia such as vaginal or oral epithelium present the same pattern of differentiation differing chiefly in the number of epithelial layers and mucous production. While the stages of squamous differentiation with their concomitant changes in gene expression are well characterized, the transcription factors that regulate differentiation-specific genes have only recently been characterized. The involucrin, the Matrix Metalloproteinase-9 (MMP-9) and Keratin 10 (K10) are well-characterized differentiation markers in keratinocytes and their promoters have been cloned. The involucrin promoter (INV) is 2500 bp and its tissue specificity is coded by a 510 bp fragment, the Matrix Metalloproteinase-9 (MMP-9) is 714 base pairs (bp) and its tissue specificity is coded by a 90 bp fragment, and the Keratin 10 (K10) is 714 bp 200 bp from mRNA start.

Generation of Nucleic Acid Composition

Nucleic acid compositions containing polypeptides of interest are designed and formulated to obtain the desired level of transfer, replication and expression efficiency of the polypeptide of interest inside the host cell. Generally, nucleic acid compositions are prepared to include a promoter, a selectable marker, and a gene of interest. In certain embodiments of the invention, SIV genes encoding for retroviral antigens were delivered into epithelial stem cells to elicit specific expression at the mucosal portal of entry surfaces. Retroviral vectors are widely used to integrate and express exogenous genes into a variety of cells and provide an efficient gene transfer tool for human gene therapy applications. These vectors have been used with considerable success for transduction of epidermal stem cells in culture and in vivo. However, transcription from the long terminal repeat (LTR) is dependent on viral promoter/enhancer elements located in the U3 region of the 5'LTR, which allow constitutive expression of the transferred gene in most cell types, including keratinocytes. Several strategies have been employed to confer tissue- or cell-specific expression to retroviral vectors. These include insertion of a tissue-specific promoter in an internal position within the retroviral vectors, construction of self-inactivating vectors, in which viral enhancer elements are deleted thereby allowing expression from the internal promoter, and insertion of a complete minigene into the LTR upstream from the U3 region. These strategies have usually resulted in decreased viral titer and have often failed to induce strict tissue-specific expression. Attempts to redirect LTR transcriptional activity by replacing the viral enhancer with heterologous control elements from cellular genes or viral genes have been successful for HIV and SIV. This strategy should allow transgene expression in a specific tissue or cell without significant loss in the viral titer as observed for non-lentiviral retroviruses. The size of tissue-specific enhancers remains a major limitation of this approach. This size should not exceed 1500 bp whereas tissue specificity is usually borne by a region larger than this size. In the case of involucrin, however, it has been possible to shorten the promoter without loss of tissue specificity by fusing the distal region of the promoter directly to the involucrin minimal promoter.

An embodiment of the invention is a nucleic acid composition designed to elicit long-term immunity against HIV infection at the entry site of the virus. This embodiment relies on the expression of viral proteins from epithelial stem cells at the basal layer of the epithelium and a promoter that is specific for terminally differentiated epithelial cells. In one embodiment, the involucrin promoter, which is exclusively expressed in terminally differentiated epithelial cells, was chosen and used to generate the desired nucleic acid composition. A GFP-tagged replication competent SIVdeltaNef and a GFP-tagged replication deficient SIVdeltaVifdeltaNef constructs under the transcriptional control of the involucrin promoter (pINV) (also referred to as pINV-SIVdeltaNef-GFP and pINV-SIVdeltaVifdeltaNef-GFP, respectively) were generated.

In Vivo Use of the Nucleic Acid Compositions

The mechanisms that control the transcription of involucrin in epidermis and mucosa are quite well conserved, as the human involucrin promoter is active in-mouse epidermis and vaginal/ectocervix epithelium. When administered intradermally to mice, the GFP-reporter gene under the transcriptional control of the involucrin promoter was found to be expressed in the upper layers of the epidermis. Although transduced cells were very low in number, high and sustained anti-GFP antibody production was observed in vivo. After production of high concentrations of infectious viral particles, the integrity of the constructs (regions encoding for GAG, POL and GFP) in the VSV-G pseudotyped viral particles was demonstrated.

In an embodiment of the invention, after infection through different mucosal routes (subcutaneous, intravaginal, or intrarectal), the pINV-SIVdeltaVifdeltaNef-GFP construct would integrate into epithelial stem cells and show long-term expression in upper layers of the epithelium even after multiple cycle of epithelia renewal. The involucrin promoter would drive the expression of the pINV-SIVdeltaVifdelta-Nef-GFP construct in terminally differentiated epithelial cells. The long-term antigen expression in upper layers of the epithelium would occur even after multiple cycles of epithelia renewal, thus eliciting a long-term immunity against HIV/SIV infection at the site of viral entry.

The present inventions will be described more fully hereinafter with reference to the accompanying drawings in which embodiments of the invention are shown. These inventions may, however, be embodied in many different forms and should not be construed as limited to the exemplary embodiments set forth herein; rather, these embodiments are provided so that this disclosure will be thorough and complete, and will fully convey the scope of the inventions to those skilled in the art.

While these embodiments have been described with emphasis on the embodiments, it should be understood that within the scope of the appended claims, the embodiments might be practiced other than as specifically described herein. Although the invention has been shown in only a few of its forms, it should be apparent to those skilled in the art that it is not so limited but susceptible to various changes without departing from the scope of the invention. Accordingly, it is intended to embrace all such alternatives, modifications, and variations as fall within the spirit and broad scope of the appended claims.

Those skilled in the art will recognize that many changes and modifications may be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, those skilled in the art may recognize that certain steps can be combined into a single step.

EXAMPLES

The following examples further illustrate the compositions and methods,

Example 1—Generation of Constructs

FIG. 1 is a schematic representation of the different constructs used as starting materials in one embodiment of the invention. FIG. 1A is a representation of the full-length SIVmac239 genome and encoding regions. FIG. 1B is a representation of 3'-half of SIVmac239 (p239SpE3') and of 5'-half of SIVmac239 (p239SpSp5') plasmids obtained from Ronal Desrosiers (NEPRC, Southborough, Mass.) used as starting material to set up the different constructs. FIG. 1C is a representation of SIVmac239-STR and SIVmac239-EF1a/STR plasmids, lacking portions of the 5'U3 regions in both LTR (termed STR for “short terminal repeat,” instead of currently used LTR for “long terminal repeats” for retroviruses), FIG. ID is a representation of SIVmac239-EF1a/STR/IRES-GFP plasmid where Nef gene has been deleted by insertion of an IRES-GFP region between positions 9500 and 9690 in SIVmac239-EF1a/STRconstruct. This insertion has been performed using the XhoI restriction site within the Nef gene by classical molecular biology methods and present in both ends of the IRES-GFP encoding region.

Example 2—Formation of Provirus

Figure 2:
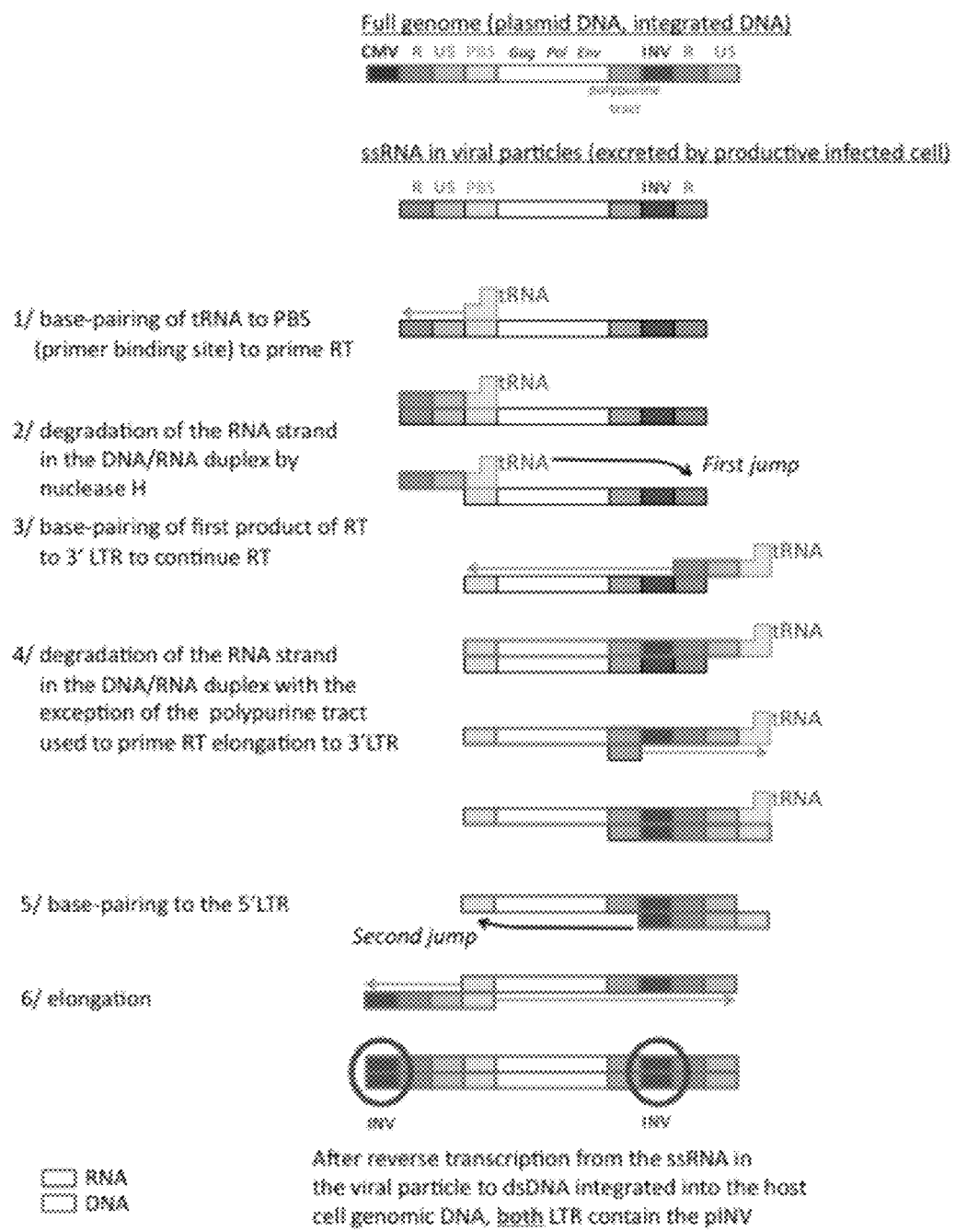
FIG. 2 is a schematic representation of the formation of pro viruses from constructs using the CMV and the involucrin promoters.

FIG. 2 is a schematic representation of the formation of proviruses from the pCMV- and the pInv-driven constructs. The full length SIV constructs were generated as plasmids containing full length 5'-LTR with the CMV promoter in lieu of their 5'-U3 region in both pCMV- and pInv-driven constructs, and either the CMV promoter or the involucrin promoter in the U3 region of their respective 3'-LTR. The messenger RNA molecules contained in the VSV-G pseudotyped viral particles after co-transfection of the full length SIV constructs with the pL/VSVG lack the pCMV promoter corresponding to the 5'-U3 region and the 5'-U5 region of both constructs. As a result of the reverse transcription and double stranded molecule formation of proviruses after infection by VSV-G pseudotyped viral particles depicted in FIG. 2, the pINV-driven construct integrated as double stranded DNA molecule and was used for SIV protein production by infected cells has both restituted complete LTR with involucrin promoter (U3 regions). Similarly, the pCMV-driven construct integrated as double stranded DNA molecule has both LTR with CMV promoter.

Example 3—In Vivo Promoter Activity Assay

Figure 3A:
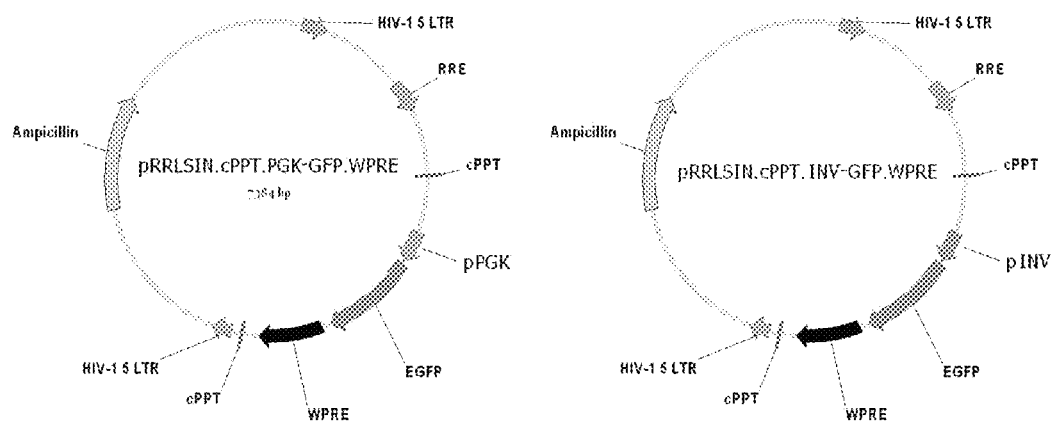
Figure 3A:
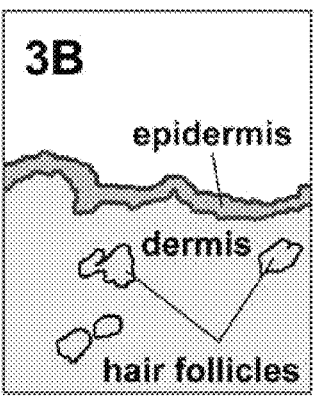
Figure 3A:
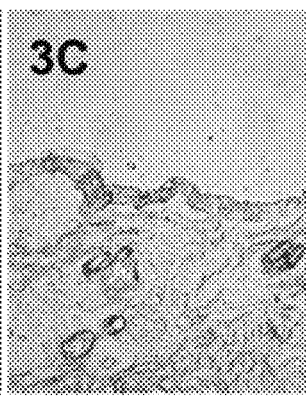
Figure 3A:
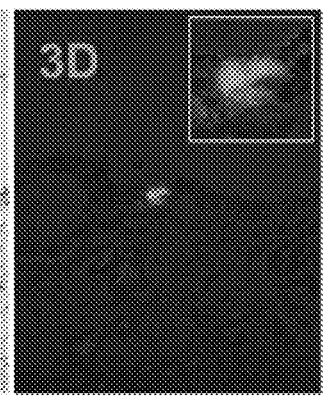

Involucrin is a well-characterized differentiation marker in keratinocytes. When used to generate transgenic mice, minimal human involucrin promoter driven construction leads to the expression of reporter gene in the upper part of epidermis. Transduction of the epidermis in mice by topical application of an involucrin promoter driven vector leads to the expression of the reporter gene into the upper strata of the epidermis. To test the efficacy of the involucrin promoter constructs of an embodiment of the current invention, in vivo promoter activity assays were performed in mice. Mice were inoculated via the epidermal route a transcriptional activity reporter plasmid where the GFP encoding region is under the transcriptional control of the involucrin minimal promoter (pRRL.SIN.cPPT.pINV-GFP.WPRE) (FIG. 3A). One week after inoculation, mice were euthanized and skin samples were frozen, prepared for histological analysis and visualized by fluorescent microscopy. As expected, GFP-expression of pRRL.SIN.cPPT.pINV-GFP.WPRE plasmid is shown in the stratum corneum of the mice epithelia following epidermic inoculation (FIGS. 3B-D). FIG. 3B is a schematic representation of the views shown in FIG. 3C (contrast microscopy of the region of interest, i.e., sample of mouse epithelium inoculated with pINV-GFP construct) and FIG. 3D (fluorescence microscopy of the same region shown in FIG. 3C).

Example 4—Eliciting an Immune Response

Figure 4:
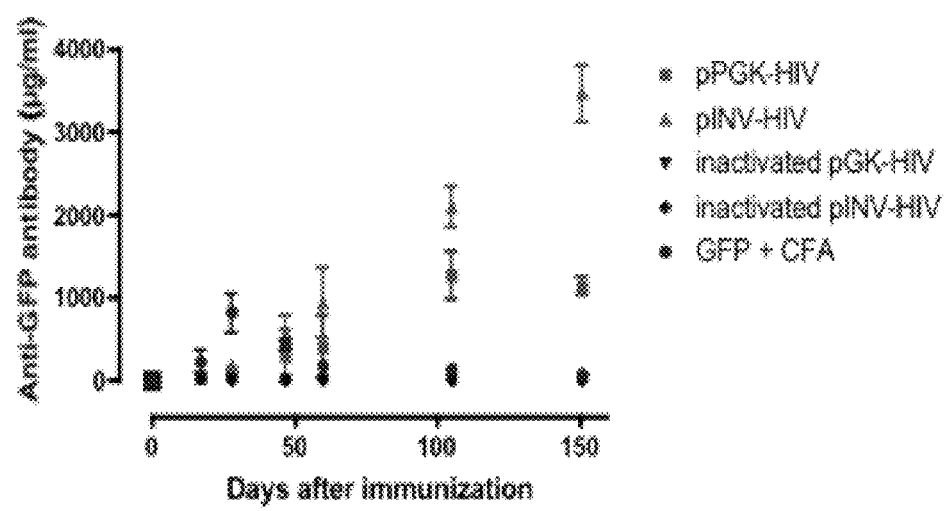
FIG. 4 is a graphical representation of the levels of anti-GFP antibodies in the mice serum at different times post-inoculation. The mice were inoculated with one of the following: involucrin promoter driven HIV vectors in the active or inactivated forms, PGK driven HIV vectors in the active or inactivated forms, and Complete Freund Adjuvant immunization.

The efficacy of the involucrin minimal promoter was evaluated by ELISA to determine the presence of anti-GFP antibodies in the mice serum at different times post inoculation as a surrogate marker for GFP expression. Significant increase in anti-GFP antibodies was detected in mice serum over time for the involucrin promoter driven vector compared to PGK promoter driven vector or to Complete Freund Adjuvant immunization (FIG. 4). These results prove that the involucrin minimal promoter used as a transcriptional regulatory element, allowed high and sustained expression of GFP in the upper layers of the epidermis.

Example 5—Construction of SIV-Derived Vectors

Figure 5:
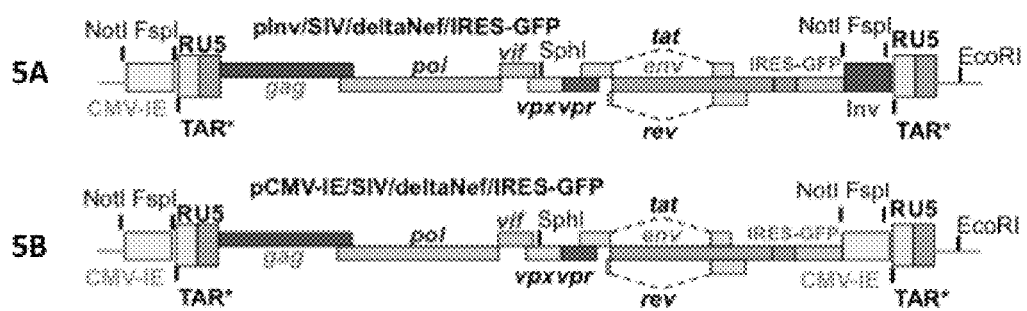
FIG. 5A and FIG. 5B are illustrations of the nucleic acid compositions that have the SIV genome constructs under the transcriptional control of the involucrin minimal promoter and the CMV promoter respectively.

An embodiment of the invention relies on the use of full length SIV genome constructs under the transcriptional control of the involucrin minimal promoter. This embodiment takes advantage of the need of attenuation of the vector by the mean of Nef gene deletion to introduce the GFP reporter gene in order to monitor the expression of these constructs in the different models. FIG. 5 is a schematic representation of the pInv/SIV/deltaNef/IRES-GFP and the pCMV-IE/SIV/deltaNef/IRES-GFP plasmids. These constructs were generated by substitution of the 5' LTR U3 region of SIVmac239-EF1a/STR/IRES-GFP construct with the CMV-IE promoter; and, by substitution of the 3' LTR U3 region of SIVmac239-EF1a/STR/IRES-GFP construct either with the human involucrin promoter (pINV) or with the CMV-IE promoter (pInv/SIV/deltaNef/IRES-GFP and pCMV-IE/SIV/deltaNef/IRES-GFP, respectively). pCMV was chosen as positive control for the different steps necessary to generate virus stocks to be used for animal inoculations (control of the infections in vitro to check the infectivity of the VSV-G pseudotyped viral particles produced after co-transfections).

Example 6—Construction of SIV-Derived Replication Deficient Vectors

Figure 6:
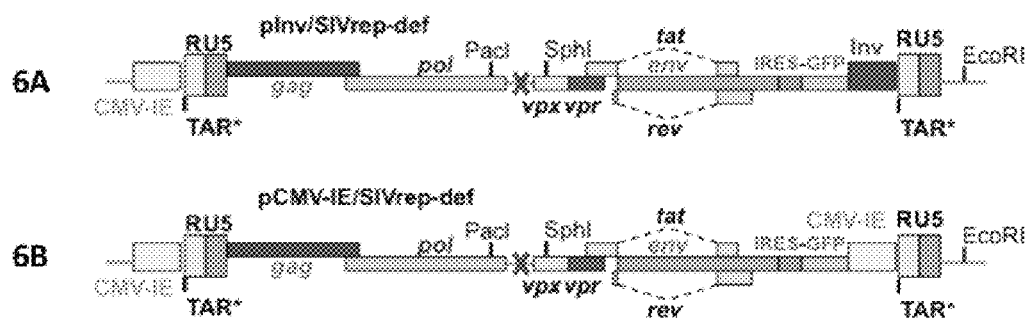
FIG. 6A and FIG. 6B are illustrations of replication deficient versions of nucleic acid compositions described in FIG. 5A and FIG. 5B, that were constructed by deleting the vif gene.
Figure 7:
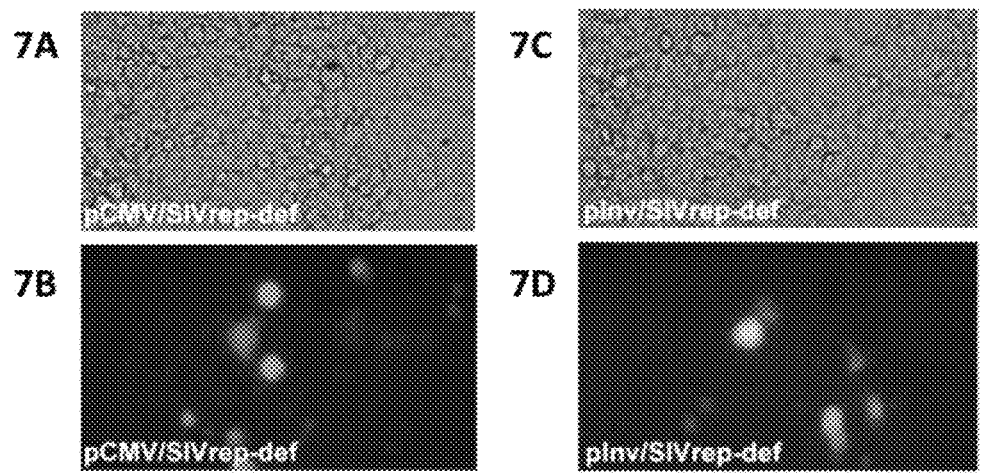
FIG. 7A and FIG. 7B are the light microscopy and fluorescence microscopy images of cells transfected with the SIV genes under the control of the CMV promoter.
FIG. 7C and FIG. 7D are the light microscopy and fluorescence microscopy images of cells transfected with the SIV genes under the control of the involucrin promoter.

In another embodiment of the invention, replication-deficient viral constructs were obtained by deleting the vif gene in the constructs referenced in Example 5. FIGS. 6A and 6B show the schematic representation of the overall generation of the mucosal SIV-derived vectors.

Example 7—In Vitro Assessment of SIV-Derived Vectors

Viral stocks of SIV-derived vector were obtained by co-transfection in HEK 293T cells of the different constructs with the plasmids as described in material and methods. Virus were pseudo-typed by Vesicular Stomatitis Virus G glycoprotein allowing the production of viral particles with significantly broadened host cell range including keratinocytes. GFP-expression was visualized 72 hours after co-transfection of the replication-deficient pCMV/SIVrep-def or, the replication-deficient pInv/SIVrep-def plasmids, with the pLP/VSVG plasmid in HEK 293T cells. Images obtained using light microscopy and fluorescence microscopy of cells transfected with the SIV genes under the control of the CMV and the involucrin promoters are shown in FIGS. 7A-7B, and FIGS. 7C-7D respectively.

Example 8—In Vitro Assessment of SIV-Derived Vectors

Figure 8:
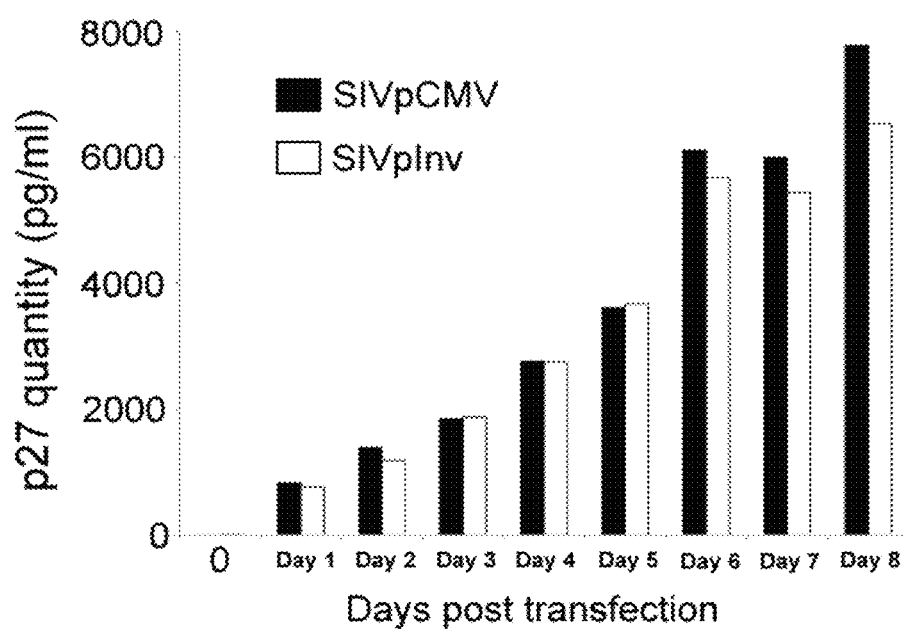
FIG. 8 is a graphical representation of the levels of expression of the p27 capsid protein up to 8 days post-transfection with both pCMV and pInv-driven constructs.

The production of VSV-G pseudotyped viral particles was assessed by monitoring the expression of p27 as a marker of viral shedding. The p27 capsid protein was used as marker for viral protein expression in the culture media using the SIV p27 Antigen Capture Assay. FIG. 8 shows the increase of the expression of p27 capsid protein up to 8 days post-transfection with both pCMV and pInv-driven constructs.

Example 9—Determination of Viral RNA

Figure 9A:
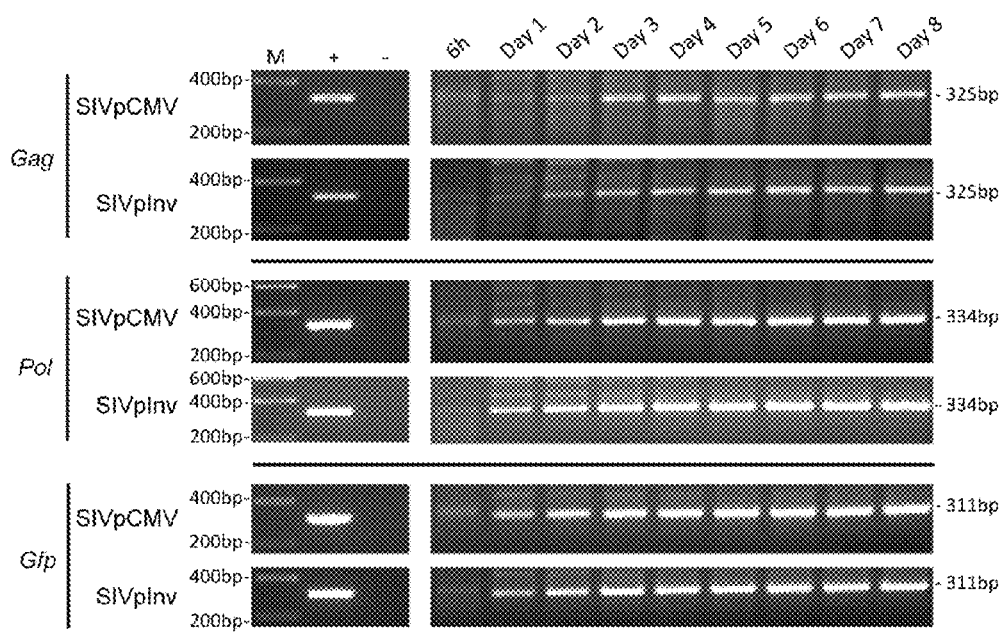
FIG. 9A is a visualization of the gels containing the PCR products amplified using primers specific for Gag, Pol and GFP genes from the culture supernatants of cells transfected with pCMV- and pInv-driven constructs.
Figure 9B:
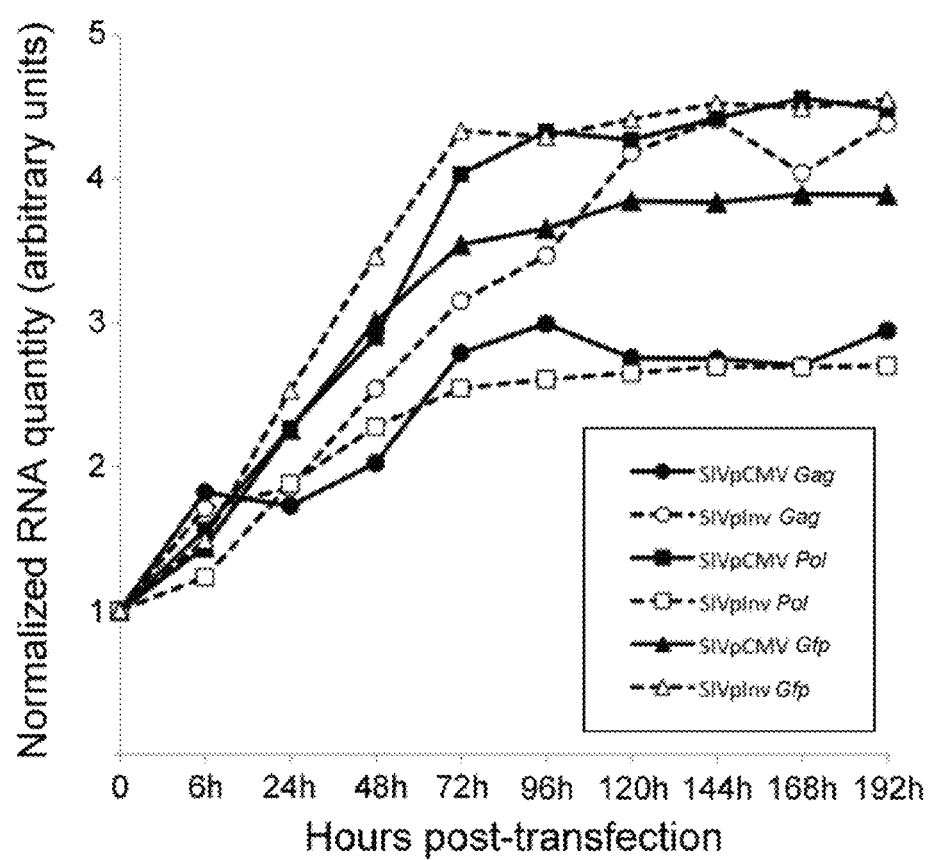
FIG. 9B is a graphical representation of the increase in amounts of PCR products shown in FIG. 9A.

To check for viral particles and ability to express SIV proteins from both constructs after infections, the presence of viral RNA was assessed in the culture supernatants. RNA was isolated from the culture supernatants and RT-PCR was performed using primers specific for the regions of the constructs encoding for genes of interest (Gag, Pol and GFP genes). FIG. 9A shows the PCR products obtained after DNase I treatment and RNA isolation from culture supernatants, followed by reverse-transcription using primers specific for Gag, Pol and GFP genes. These results demonstrated the integrity of the constructs within these regions with a marked increase of RNA in the culture supernatants up to 8 days post-transfections with both pCMV- and pInv-driven constructs. FIG. 9B shows the quantification of the PCR products shown in FIG. 9A and assessed by classic quantification method using Adobe Photoshop software. Viral particles contained in the culture media 5 days post-transfection were concentrated using a KrosFlo Research Iii Tangential Flow Filtration System (SpectrumLabs) or classic centrifugation method using Centricon Plus-70 units (Millipore) for small starting volumes. The quantification of the viral particles before and after concentration was performed by titration of p27 in the different suspensions using the SIV p27 Antigen Capture Assay.

In these examples, the p27 titration of the culture media before concentration was ~6 ng/ml for both constructs. After concentration by centrifugation, viral stocks were established with a p27 concentration of 35 ng/ml (SIVpCMV construct) and 90 ng/ml (SICpInv construct), thus concentrating the initial viral stocks from producing cells up to ~15 times.

Example 10—Transduction of Human Keratinocytes with SIV-Derived Vector

Figure 10A:
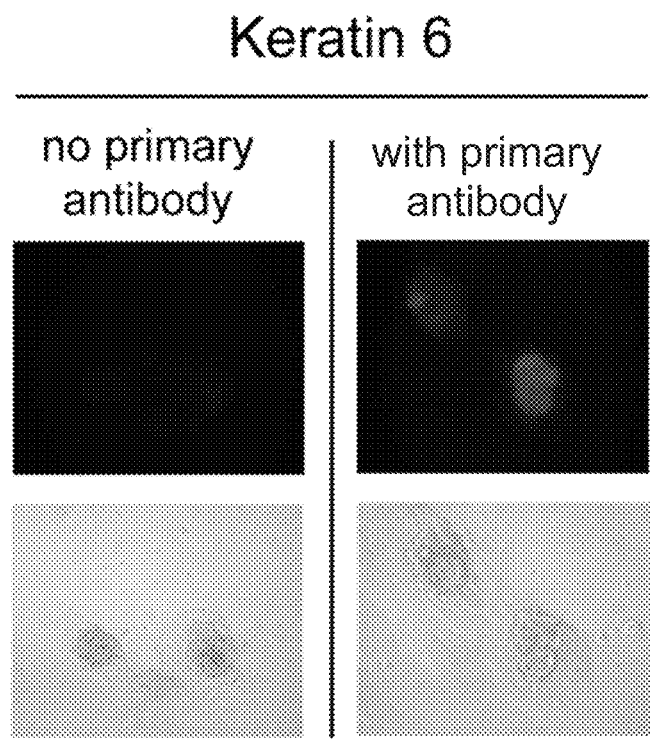
Figure 10B:
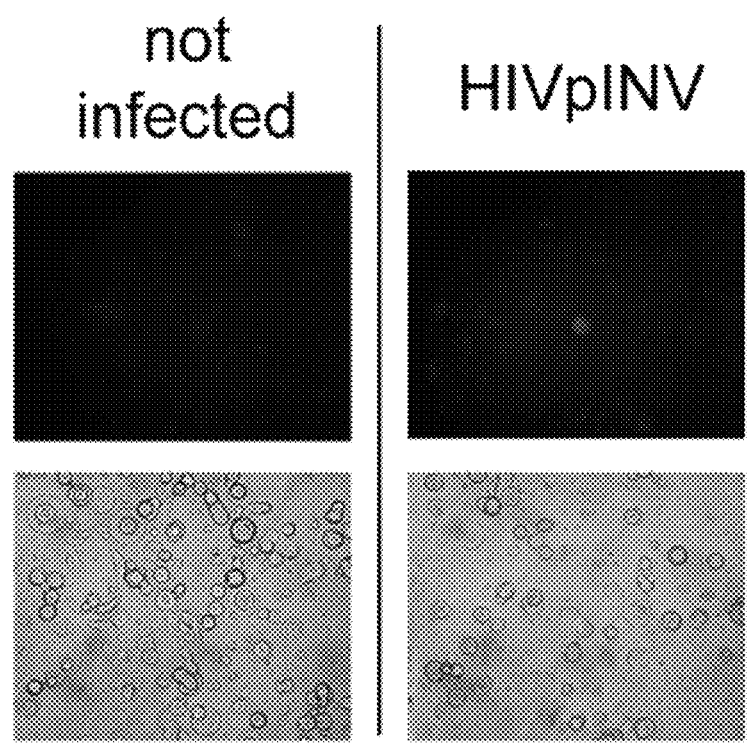
Figure 10C:
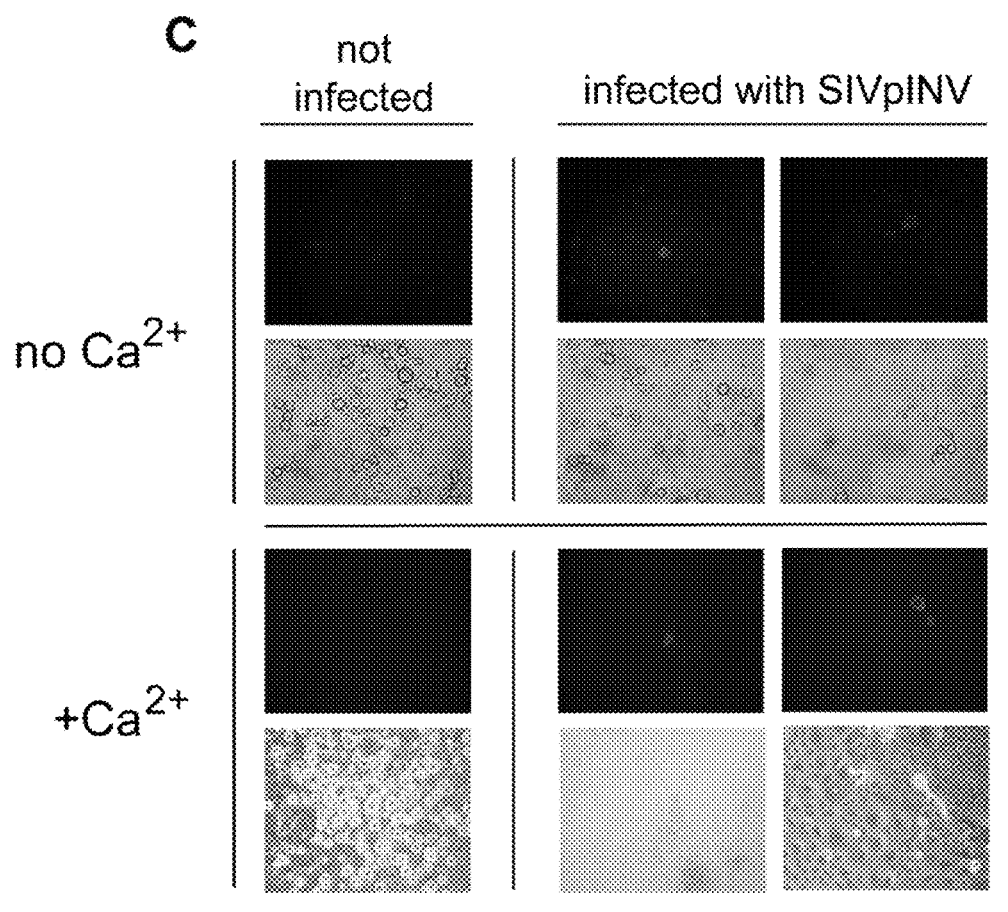
Figure 10D:
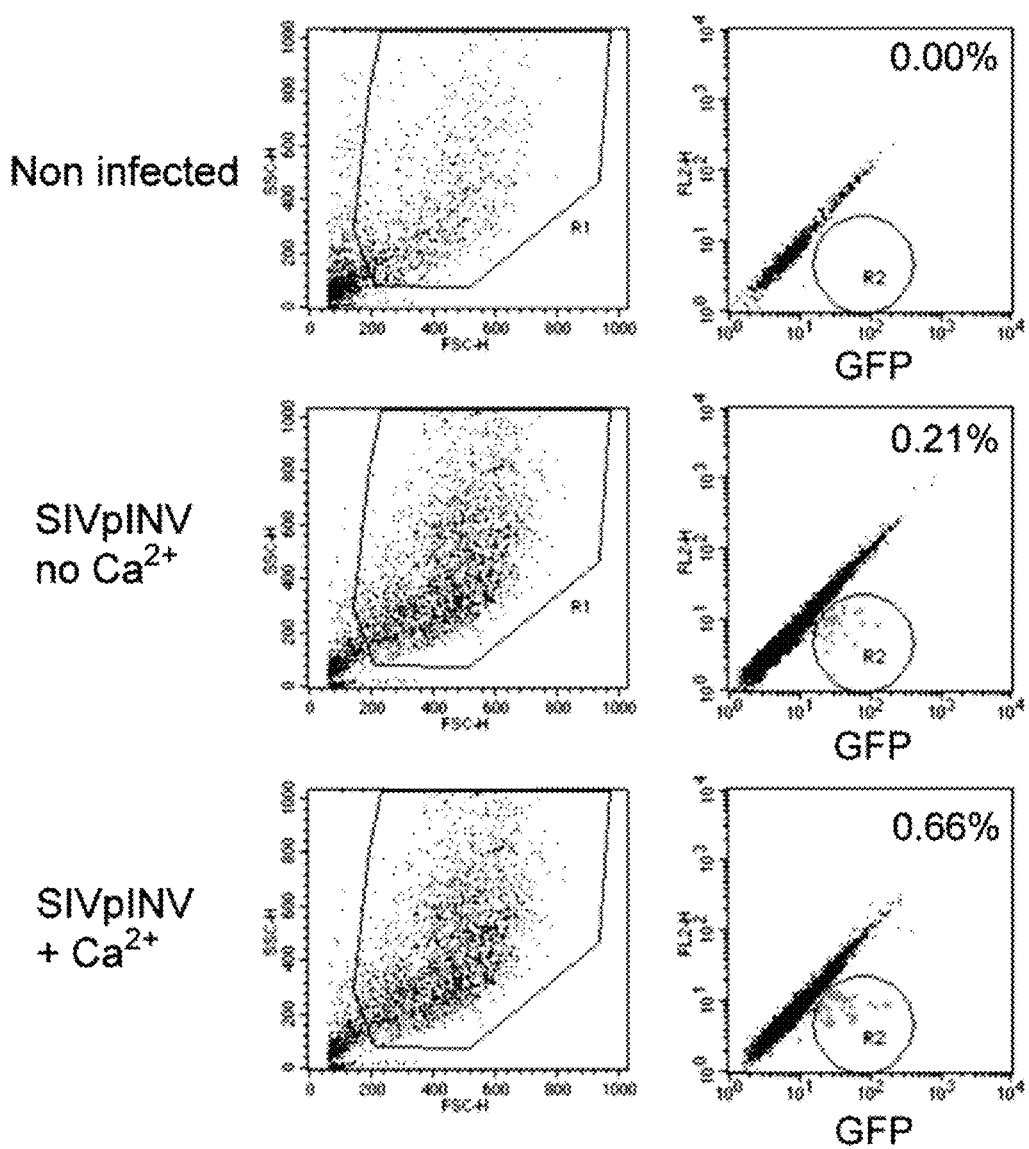

Infectious viral particles obtained by co-transfections of HEK 293 T cells with pInv/SIV/deltaNef/IRES-GFP construct and pLP/VSVG plasmid were used in transduction experiments in normal human epidermal keratinocytes (NHEK). In these conditions, stem cells divide and few of them (up to 10%) differentiate spontaneously. Addition of 1 mM of calcium in the culture media stopped cell division and induced a massive cell terminal differentiation of stem cells into keratinocytes. The involucrin minimal promoter in SIV-derived vector was able to drive GFP expression in NHEK. To this aim NHEK cells were transfected with Involucrin promoter driven HIV vector (noted HIVpInv) used in mice. GFP expression was detected in these cells (FIG. 10B). When those cells were infected with the SIV-derived vector, GFP expression was detected by fluorescent microscopy (FIG. 10C) or flow cytometry (FIG. 10D). Interestingly, the percentage of cells expressing the green fluorescent protein significantly increased with the addition of calcium in the culture media, suggesting an increase in viral protein expression upon keratinocyte differentiation. These data demonstrate the ability of an SIV vector under the control of the Involucrin promoter to drive and increase gene expression in keratinocytes upon their differentiation.

Example 11—Schematic Representation of the Vaccine Approach

Figure 11:
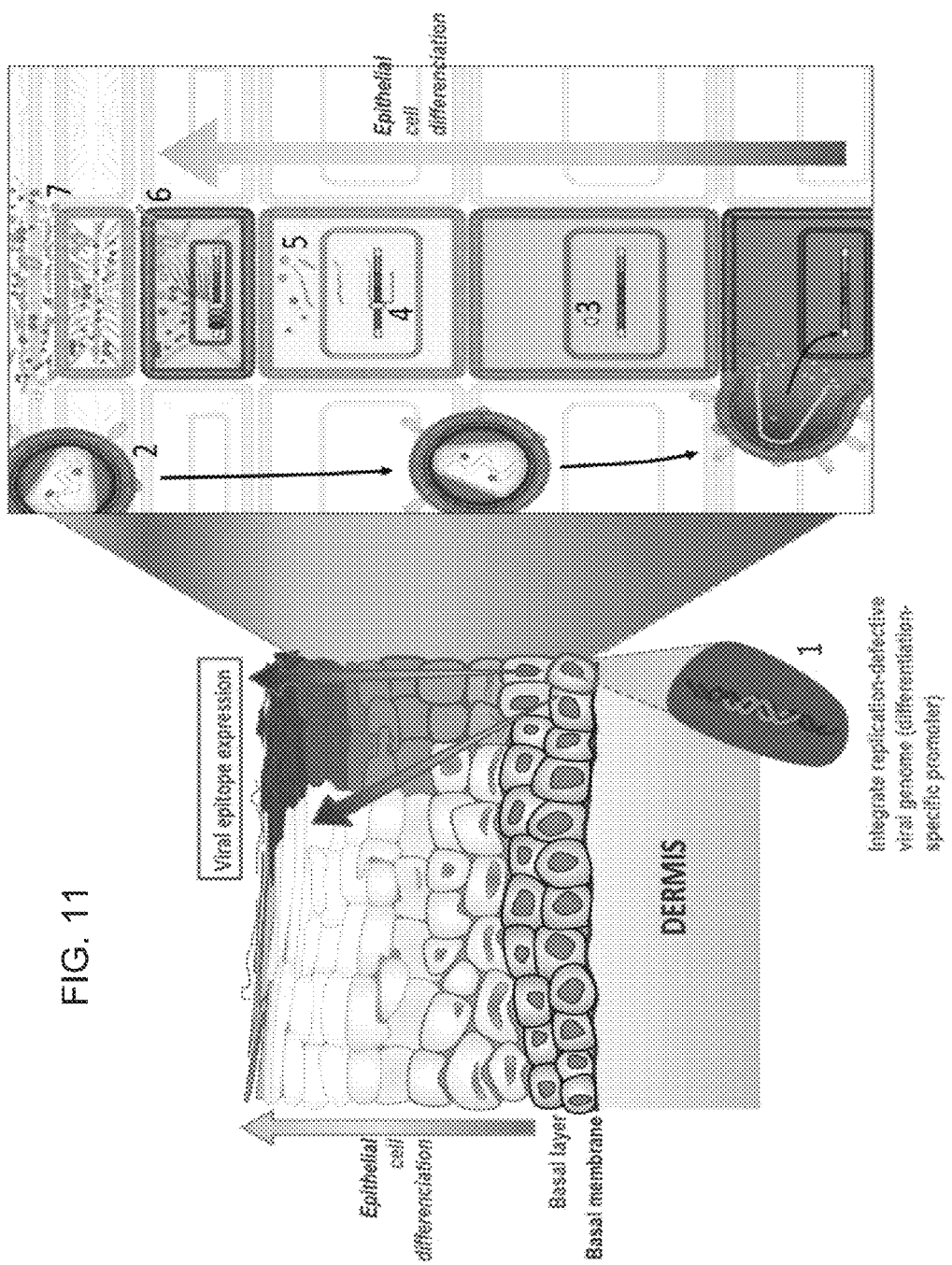
FIG. 11 is an exemplary illustration of the vaccine strategy utilizing the replication-defective viral genome under the control of a differentiation-stage specific promoter like involucrin.

After integration of the Involucrin-driven viral constructs into basal layer stem cells (1), these cells will divide and differentiate triggering SIV antigens expression in the upper corneal layers of the epidermis. The level of SIV antigens expression is represented by the darkening green shades on the FIG. 11 (left panel), from the basal layer stem cells (blue shade, black line) to the differentiated epidermal cells of the epithelia stratum corneum (dark green shade, red line). Arrows depict the orientation of the cells differentiation. The expression of SIV antigens will be transcriptionally regulated by the Involucrin promoter, and will be depending on the differentiation of the epidermal cells of the epithelia stratum corneum. The right panel of the FIG. 11 shows the overall schematic representation of the vaccine approach. VSV-G pseudotyped viral particles containing the Involucrin-driven SIV construct is used as vector to target basal stem cells (2). As the basal stem cells divide to generate the epithelia, the epithelia cells are differentiating. The Involucrin promoter is composed of binding sites for transcription factors (3) that drive the expression of the Involucrin that is expressed in differentiated epithelial cells. Similarly, the Involucrin promoter of the Involucrin-driven SIV constructs will control the transcription of SIV genes (4) thus leading to the expression of SIV proteins/antigens (5) upon epithelial cell differentiation. Differentiated cells of the upper layers of the epithelia are expressing SIV proteins/antigens that are continuously exposed by the differentiated epithelial cells (6) and released at the mucosa upon stratum corneum cell death and breakdown (7), thus eliciting long lasting immunity.

Example 12—General Methods

The following methods, materials, and procedures are intended to be exemplary and are not intended to limit the scope of the invention.
Construction Designs Recombinant DNA plasmids and vaccine vectors were built using NEB restriction endonucleases and ligations performed using Ligafast Rapid DNA Ligation protocol (3U ligase in 10 ml final reaction volume). OneShot TOP10 Chemically Competent *E. coli* (InVitrogen, USA) was routinely used for plasmid DNA amplification. Bacteria were routinely grown in Luria Broth (LB). Ampicillin was used at a final concentration of 100 µg/ml. Productions of plasmids were carried out using Qiagen EndoFree Plasmid Mega Kits.
Construction of Involucrin Promoter-Driven Vectors The minimal Involucrin promoter was synthesized by overlapping PGR, as defined in S. Ghazizadeh, C. Doumeng, and L. B. Taichman in *Durable and stratum-specific gene expression in epidermis*. Gene Therapy, 2002. 9(19): p. 1278-85. This promoter was then introduced into the pRRL.SIN.cPPT.pPGK-GFP.WPRE plasmid kindly provided by Dr. Didier Trono (EPFL, Lausanne, Suisse) by replacement of the pPGK promoter by the involucrin minimal promoter at the Cla-I BamH-I restriction sites. Embodiments of the invention include the involucrin promoter as described by SEQ ID NO: 001. Other embodiments may include nucleic acid compositions that contain biologically functional equivalents of the involucrin promoter.
Construction of SIV Vaccine With respect to the generation of recombinant SIV vaccine described in this study, the IRES-GFP fragment from pBlueScript IRES-GFP plasmid (Invitrogen) was amplified by PGR using specific primers containing XhoI restriction sites and cloned into the SIVmac239megalo3' plasmid between positions 9500 and 9690 to generate the pSIVmac239megalo3'/IRES-GFP plasmid. The remaining of Nef gene was deleted by introducing the STR fragment from pSIVmac239/STR plasmid between the EcoR-I/Not-I restriction sites in pSIVmac239megalo5' plasmid and Not-I/Nhe-I restriction sites in pSIVmac239megalo3'/IRES-GFP plasmid which gives rise to pSIVmac239megalo/STR5' and pSIVmac239megalo/STR3'/IRES-GFP respectively. To avoid the TAR/Tat transcriptional control, the TAR sequence was inactivated by homology to HIV using the following primers: [SEQ ID NO: 005] 5'-GCGGCCGCTGCGCA-GAGGCAGAAAGAGCCATTGGAGGTTCTCTCCAG- CACTA GC and [SEQ ID NO.: 006] 5'-AGGAGGAGCAT-TGGTGTTCCCTGCTAGACTCTCACC. This fragment was subcloned and introduced at the Fsp-I and Nar-I sites of pSIVmac239megalo/STR5' and pSIVmac239megalo/STR3'/IRES-GFP plasmids. These plasmids are named pSIVmegaloSTR5'/TAR* and pSIVmegaloSTR3'IRES-GFP/TAR*. Finally full-length construct was reconstituted after ligation of its both 5'- and 3'-halves together. This ubiquitously transcriptionally regulated construct was named pCMV-IE/SIV/deltaNef/IRES-GFP.

Identically, a viral construct was generated that was expressed in the differentiated upper layers of the epithelia using the involucrin promoter designed as described herein. The 570 bp involucrin promoter was cloned in place of the 5'-CMV promoter of the pSIVmac239megalo5' plasmid (NotI/FspI restriction sites) and pSIVmac239megalo3' (NotI/FspI restriction sites). Full-length construct was reconstituted after ligation of its both 5'- and 3'-halves. This differentiated epithelia-specific transcriptionally regulated construct was named pInv/SIV/deltaNef/IRES-GFP.

To obtain replication-deficient viral constructs, vif gene from the 5' moiety of pCMV-IE/SIV/deltaNef/IRES-GFP and pInv/SIV/deltaNef/IRES-GFP plasmids (pSP72 backbone) were deleted by substitution of their PacI/SphI fragment with the PacI/SphI fragment of pSIVdeltaVif5' provided by Ron Desrosiers. The resulting recombinant plasmids were named pCMV/SIV5'/deltaVif and pInv/SIV5'/deltaVif. Full-length constructs were obtained by ligation of either the 3' moiety of pCMV-IE/SIV/deltaNef/IRES-GFP or pInv/SIV/deltaNef/IRES-GFP plasmids (SphI/EcoRI). For simplification, the full-length replication-deficient viral constructs were named pCMV/SIVrep-def (pCV/SIV/deltaVif/deltaNef/IRES-GFP) and pInv/SIVrep-def (pInv/SIV/deltaVif/deltaNef/IRES-GFP).

CFA Immunization and Viral Transduction of Epidermis

Mice were immunized by footpad subcutaneous injection of emulsified complete Freund's Adjuvant (CFA) with 200 μg of His-tagged purified GFP in PBS (1:1 by volume). Viral transduction in mice was performed as already described. Briefly, FVB mouse shaved backs were dermabraded using a felt wheel. The wound thus created was allowed to remain open to the air. On day 3 after abrasion, 50 μl (containing 10e8 c.f.u.) of VSV-pseudotyped pRRL.SIN.cPPT.pINV-GFP.WPRE or pRRL.SIN.cPPT.pGK-GFP.WPRE were deposited into the compartment located between the scab and the healing tissue surface.

Histological Analysis

At day 7 post-inoculation, mice were sacrificed and the part of the skin that have received the inoculum were snap frozen in OCT compound. Eight μm cryosections were fixed for 10 min in 4% paraformaldehyde, rinsed in PBS and examined by fluorescent microscopy.

Anti-GFP Antibody Quantitation in Mice Serum

The quantitation of anti-GFP antibodies in the mice serum was evaluated by ELISA using an in house recombinant GFP protein to establish a checkerboard titration. An in-house ELISA was developed using recombinant GFP protein coated on maxisorp plates (Nalge Nunc, Rochester, USA) in a 1.5 mM carbonate/bicarbonate buffer of pH 9.6. The serum was diluted 100- to 500-fold and incubated for an hour at room temperature in a 1.5 mM carbonate/bicarbonate buffer. Anti-GFP immunoglobins were quantitated after incubation at room temperature for one hour with horse radish peroxidase linked goat anti-mouse Ig kappa light chain antibodies, and subsequent color development.

Human Keratinocytes Culture and Differentiation

Normal Human Epidermal Keratinocytes (NHEK) from juvenile foreskin were obtained from PromoCell (Heidelberg, Germany) and culture with keratinocyte growth medium 2 (PromoCell, Heidelberg, Germany) according to manufacturer instructions on fibronectin-coated pates (Merck Millipore, Darmstadt, Germany). For terminally differentiation of NHEK 1 mM concentration of CaCl2 (PromoCell, Heidelberg, Germany) was used. Clone 16B4 was used for cytokeratin-6 antibody detection.

Quantification of GFP-Expression

Light and fluorescent microscopy were performed using a Zeiss microscope. Flow cytometry experiments were performed on FACSCalibur (CellQuest software). GFP-expression was quantified by flow cytometry using in parallel two batches with or without calcium.

Viral Stock Production

HEK-293 cells were maintained as adherent cultures in DMEM supplemented with 10% FBS and 500 ug/ml Geneticin. HEK-293 cell cultures (75 $cm^2$ flasks) were co-transfected with 15 ug of each plasmid pCMV-IE/SIV/deltaNef/IRES-GFP and pLP/VSVG (Invitrogen) or pInv/SIV/deltaNef/IRES-GFP and pLP/VSVG, using Lipofectamine 2000 according to manufacture protocol (Invitrogen). Co-transfection using VSVG plasmid encoding for envelope G glycoprotein from VSV, produced pseudotyped retrovirus with a broader range of infectable cell types. After overnight incubation, the media was changed and cells allowed to incubate for an additional 48 hours. The media containing the virus was removed, passed thru a 0.45 micron filter, and concentrated using a MiniKrosFlo Research II Tangential Flow Filtration System. A polyethersulfone hollow fiber membrane module was used with a 500 Kd molecular weight cutoff. Titration of p27, before and after concentration, was determined using the SIV p27 Antigen Capture Assay (Advanced Bioscience Laboratories) according to the manufacturer instructions.

Reverse-Transcription and Quantification of RNA in Culture Supernatants

Total RNA from culture supernatants was purified using the QIAamp Viral RNA Mini Kit (Qiagen) according to the manufacturer instructions. Briefly, 140 μl of culture supernatants were used as starting material and RNA was eluted in 50 μl elution buffer. This material was then DNase-treated using Turbo DNase (Ambion) according to the manufacturer instructions in 300 μl reaction volume. After incubation at 37° C. for 30 mn, DNase was removed by addition of equal volume of Phenol-Chloroform saturated solution, pH5.2 (MP Biochemicals) and RNA ethanol-precipitated from the aqueous phase using 20 μg glycogen as carrier (EMD Millipore), The RNA pellet was air-dried before resuspension in 10 μl nuclease-free water. 2 μl of RNA was then used as starting material for reverse-transcription using SMART-Scribe Reverse Transcriptase (Clontech) in a final reaction volume of 10 μl according to the manufacturer instructions and using a Gag gene specific primer for reverse transcription (B014: [SEQ ID NO: 007] 5'-gggccgggacagaaggctaga-3'). PCR was performed using 1 ul of reverse transcription reaction as template and the Phusion High Fidelity DNA Polymerase with GC Buffer (NEB) for a final reaction volume of 12.5 μl according to the manufacturer instructions. The primers used for the PCR reactions were as follows: for Gag gene, sense primer B014: [SEQ ID NO: 008] 5'-gggccgggacagaaggctaga-3', antisense primer B015: [SEQ ID NO: 009] 5'-cctctgggggagcagttggca-3', for Pol gene, sense primer B016: [SEQ ID NO: 010] 5'-gcatggtgggcagggatagagc-3', antisense primer B017: [SEQ ID NO: 011] 5'-gctcaccgggtcccttccac-3', for Gfp gene, sense primer B012: [SEQ ID NO: 012] 5'-acggcgacgtaaacggccac-3' and antisense primer B013: [SEQ ID NO: 013] 5'-cggttcaccagggtgtcgcc-3'. PCR cycling was the following: initial denaturation at 98° C. for 2 mn, followed by 30 cycles with denaturation at 98° C. for 10 s and annealing/elongation at 72° C. for 45 s, and final elongation at 72° C. for 10 mn. The 12.5 µl PCR reaction volumes were run on 2% agarose gel and PCR amplicons quantified using Adobe Photoshop software.

Titration of p27 in Culture Supernatants

Titration of p27 in culture supernatants have been performed using the SIV p27 Antigen Capture Assay (Advanced Bioscience Laboratories) according to the manufacturer instructions.

While these embodiments have been described with emphasis on the embodiments, it should be understood that within the scope of the appended claims, the embodiments might be practiced other than as specifically described herein. Although the invention has been shown in only a few of its forms, it should be apparent to those skilled in the art that it is not so limited but susceptible to various changes without departing from the scope of the invention. Accordingly, it is intended to embrace all such alternatives, modifications, and variations as fall within the spirit and broad scope of the appended claims.

The present application relates to, claims the benefit of, and claims priority to U.S. Provisional Patent Application Ser. No. 61/632,431, filed Oct. 24, 2012, and U.S. Provisional Patent Application Ser. No. 61/793,658, filed Mar. 15, 2013, both of which are incorporated herein in their entireties.

Those skilled in the art will recognize that many changes and modifications may be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, those skilled in the art may recognize that certain steps can be combined into a single step.

The invention claimed is:

1. A nucleic acid composition comprising a retrovirus-based expression cassette containing:
   an involucrin promoter;
   a gene encoding an envelope protein of a human immunodeficiency virus;
   two short terminal repeat sequences; and
   no functional vif gene sequence; wherein
      the involucrin promoter controls expression of the gene encoding the envelope protein of the human immunodeficiency virus in a differentiated mucosal epithelial layer in a subject; and
      the two short terminal repeat sequences are retroviral long terminal repeat sequences lacking U3 regions.

2. The nucleic acid composition of claim 1, wherein the differentiated mucosal epithelial layer is a vaginal epithelial layer.

3. The nucleic acid composition of claim 1, wherein the differentiated mucosal epithelial layer is a rectal epithelial layer.

4. The nucleic acid composition of claim 1, wherein the differentiated mucosal epithelial layer is in an oral cavity.

5. The nucleic acid composition of claim 1, wherein the differentiated mucosal epithelial layer is in a nasal cavity.

6. A nucleic acid composition comprising a retrovirus-based expression cassette containing:
   an involucrin promoter;
   a gene encoding an envelope protein of a human immunodeficiency virus;
   two short terminal repeat sequences; and
   no vif gene sequence; wherein
      the involucrin promoter controls expression of the gene encoding the envelope protein of the human immunodeficiency virus in a vaginal epithelial layer in a subject; and the two short terminal repeat sequences are retroviral long terminal repeat sequences lacking U3 regions.

7. The nucleic acid composition of claim 6, wherein the retrovirus-based expression cassette is derived from a simian immunodeficiency virus (SIV).

8. The nucleic acid composition of claim 6, wherein the retrovirus-based expression cassette further contains no nef gene sequence.

9. A nucleic acid composition comprising a retrovirus-based expression cassette containing:

a promoter being selected from the group consisting of an involucrin promoter, a matrix metalloproteinase-9 promoter, a keratin-10 promoter, and a loricrin promoter;

a gene encoding an envelope protein of a human immunodeficiency virus;
two short terminal repeat sequences; and
no functional vif gene sequence; wherein
 the promoter controls expression of the gene encoding the envelope protein of the human immunodeficiency virus in a differentiated epithelial layer in a subject; and
 the two short terminal repeat sequences are retroviral long terminal repeat sequences lacking U3 regions.

10. The nucleic acid composition of claim 9, wherein the differentiated epithelial layer is a vaginal epithelial layer.

11. The nucleic acid composition of claim 9, wherein the differentiated epithelial layer is a rectal epithelial layer.

12. The nucleic acid composition of claim 9, wherein the differentiated epithelial layer is in an oral cavity.

13. The nucleic acid composition of claim 9, wherein the differentiated epithelial layer is in a nasal cavity.

14. The nucleic acid composition of claim 9, wherein the retrovirus-based expression cassette is derived from a simian immunodeficiency virus (SIV).

15. The nucleic acid composition of claim 9, wherein the retrovirus-based expression cassette further contains no nef gene sequence.

* * * * *